US010513541B2

(12) United States Patent
Li et al.

(10) Patent No.: US 10,513,541 B2
(45) Date of Patent: Dec. 24, 2019

(54) MUTANT OF L1 PROTEIN OF HUMAN PAPILLOMAVIRUS TYPE 11

(71) Applicants: Xiamen University, Xiamen, Fujian Province (CN); Xiamen Innovax Biotech Co., Ltd., Xiamen, Fujian (CN)

(72) Inventors: Shaowei Li, Xiamen (CN); Daning Wang, Xiamen (CN); Xinlin Liu, Xiamen (CN); Zhihai Li, Xiamen (CN); Jun Zhang, Xiamen (CN); Ningshao Xia, Xiamen (CN)

(73) Assignees: Xiamen University, Xiamen, Fujian Province (CN); Xiamen Innovax Biotech Co., Ltd., Xiamen, Fujian (CN)

( * ) Notice: Subject to any disclaimer, the term of this patent is extended or adjusted under 35 U.S.C. 154(b) by 0 days.

(21) Appl. No.: 15/781,328

(22) PCT Filed: Dec. 2, 2016

(86) PCT No.: PCT/CN2016/108349
§ 371 (c)(1),
(2) Date: Jun. 4, 2018

(87) PCT Pub. No.: WO2017/092711
PCT Pub. Date: Jun. 8, 2017

(65) Prior Publication Data
US 2019/0062379 A1 Feb. 28, 2019

(30) Foreign Application Priority Data

Dec. 4, 2015 (CN) .......................... 2015 1 0887801

(51) Int. Cl.
| | |
|---|---|
| *C07K 14/025* | (2006.01) |
| *A61K 39/12* | (2006.01) |
| *C07K 14/005* | (2006.01) |
| *C12P 21/02* | (2006.01) |
| *A61P 31/20* | (2006.01) |
| *A61P 35/00* | (2006.01) |
| *A61K 39/00* | (2006.01) |

(52) U.S. Cl.
CPC ............ *C07K 14/005* (2013.01); *A61K 39/12* (2013.01); *A61P 31/20* (2018.01); *A61P 35/00* (2018.01); *C07K 14/025* (2013.01); *C12P 21/02* (2013.01); *A61K 2039/5258* (2013.01); *A61K 2039/55505* (2013.01); *C12N 2710/20022* (2013.01); *C12N 2710/20023* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS

| | | | | |
|---|---|---|---|---|
| 5,738,853 A | * | 4/1998 | Ludmerer | A61K 39/12 424/178.1 |
| 5,795,754 A | | 8/1998 | Ludmerer et al. | |
| 6,689,366 B1 | | 2/2004 | Jansen et al. | |
| 2010/0291141 A1 | * | 11/2010 | Zhang | A61K 39/12 424/204.1 |

FOREIGN PATENT DOCUMENTS

| | | |
|---|---|---|
| CN | 1185810 | 6/1998 |
| CN | 101343314 | 1/2009 |
| CN | 101343315 | 1/2009 |
| CN | 102747047 | 10/2012 |
| WO | 96/30520 | 10/1996 |
| WO | 00/35478 | 6/2000 |

OTHER PUBLICATIONS

Hines et al. The expressed L1 proteins of HPV-1, HPV-6, and HPV-11 display type-specific epitopes with native conformation and reactivity with neutralizing and nonneutralizing antibodies. Pathobiology. 1994;62(4):165-71.*
Ludmerer, Steven W. et al, HPV11 Mutant Virus-like Particles Elicit Immune Responses That Neutralize Virus and Delineate a Novel Neutralizing Domain; Virology, 2000, 237-245; 266.
McClements, William L. et al., A Novel Human Papillomavirus Type 6 Neutralizing Domain Comprising Two Discrete Regions of the Major Capsid Protein L1; Virology, 2001, 262-268; 289.
International Search Report for PCT/CN2016/108349 dated Feb. 23, 2017.
Hines, Jeffrey F., et al., The Expressed L1 Proteins of HPV-1, HPV-6, and HPV-11 Display Type-Specific Epitopes with Native Conformation and Reactivity with Neutralizing and Nonneutralizing Antibodies, Pathobiology 1994; 62; 165-171.

* cited by examiner

*Primary Examiner* — Nianxiang Zou
(74) *Attorney, Agent, or Firm* — Honigman LLP; Thomas A. Wootton, Esq.; Jonathan P. O'Brien

(57) ABSTRACT

Disclosed are a mutated HPV11 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV11 and HPV6), and therefore can be used to prevent infection by said at least two HPV types, and a disease caused by said infection, such as cervical cancer and condyloma acuminatum. Also disclosed is use of the protein and the virus-like particle in the manufacture of a pharmaceutical composition or a vaccine for preventing infection by said at least two HPV types, and a disease caused by said infection, such as cervical cancer and condyloma acuminatum.

19 Claims, 9 Drawing Sheets

Specification includes a Sequence Listing.

SEQUENCE LISTING

<160> NUMBER OF SEQ ID NOS: 37

<210> SEQ ID NO 1
<211> LENGTH: 501

```
<212> TYPE: PRT
<213> ORGANISM: Artificial Sequence
<220> FEATURE:
<223> OTHER INFORMATION: HPV11

<400> SEQUENCE: 1

Met Trp Arg Pro Ser Asp Ser Thr Val Tyr Val Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Arg Leu Leu Ala Val Gly His Pro Tyr
                35                  40                  45

Tyr Ser Ile Lys Lys Val Asn Lys Thr Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
                100                 105                 110

Gly Val Ser Gly His Pro Leu Leu Asn Lys Tyr Asp Asp Val Glu Asn
                115                 120                 125

Ser Gly Gly Tyr Gly Gly Asn Pro Gly Gln Asp Asn Arg Val Asn Val
130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
                180                 185                 190

Gln Asp Gly Asp Met Val Asp Thr Gly Phe Gly Ala Met Asn Phe Ala
                195                 200                 205

Asp Leu Gln Thr Asn Lys Ser Asp Val Pro Leu Asp Ile Cys Gly Thr
210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
                260                 265                 270

Leu Val Lys Gly Gly Asn Asn Arg Ser Ser Val Ala Ser Ser Ile Tyr
            275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
                340                 345                 350

Asn Ser Asp Tyr Lys Glu Tyr Met Arg His Val Glu Glu Phe Asp Leu
            355                 360                 365

Gln Phe Ile Phe Gln Leu Cys Ser Ile Thr Leu Ser Ala Glu Val Met
    370                 375                 380
```

```
Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
            405                 410                 415

Val Gln Ser Gln Ala Ile Thr Cys Gln Lys Pro Thr Pro Glu Lys Glu
        420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Arg Thr Ser Ala Arg Thr Gly Ile
465                 470                 475                 480

Lys Arg Pro Ala Val Ser Lys Pro Ser Thr Ala Pro Lys Arg Lys Arg
            485                 490                 495

Thr Lys Thr Lys Lys
            500

<210> SEQ ID NO 2
<211> LENGTH: 500
<212> TYPE: PRT
<213> ORGANISM: Artificial Sequence
<220> FEATURE:
<223> OTHER INFORMATION: HPV6

<400> SEQUENCE: 2

Met Trp Arg Pro Ser Asp Ser Thr Val Tyr Val Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240
```

```
Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
            325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
            405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
450                 455                 460

Leu Gln Ser Gly Tyr Arg Gly Arg Ser Ser Ile Arg Thr Gly Val Lys
465                 470                 475                 480

Arg Pro Ala Val Ser Lys Ala Ser Ala Ala Pro Lys Arg Lys Arg Ala
            485                 490                 495

Lys Thr Lys Arg
            500

<210> SEQ ID NO 3
<211> LENGTH: 498
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<223> OTHER INFORMATION: HPV11N4

<400> SEQUENCE: 3

Met Ser Asp Ser Thr Val Tyr Val Pro Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Ser Arg Leu Leu Ala Val Gly His Pro Tyr Tyr Ser Ile
        35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80
```

```
Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
    130                 135                 140

Tyr Lys Gln Thr Gln Leu Cys Met Val Gly Cys Ala Pro Pro Leu Gly
145                 150                 155                 160

Glu His Trp Gly Lys Gly Thr Gln Cys Ser Asn Thr Ser Val Gln Asn
                165                 170                 175

Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
        195                 200                 205

Thr Asn Lys Ser Asp Val Pro Leu Asp Ile Cys Gly Thr Val Cys Lys
    210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
    290                 295                 300

Tyr Trp Leu Gln Lys Ala Gln Gly His Asn Asn Gly Ile Cys Trp Gly
305                 310                 315                 320

Asn His Leu Phe Val Thr Val Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
    370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys
```

<210> SEQ ID NO 4
<211> LENGTH: 496
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<223> OTHER INFORMATION: HPV6N5

<400> SEQUENCE: 4

```
Met Asp Ser Thr Val Tyr Val Pro Pro Asn Pro Val Ser Lys Val
1               5                   10                  15

Val Ala Thr Asp Ala Tyr Val Thr Arg Thr Asn Ile Phe Tyr His Ala
            20                  25                  30

Ser Ser Ser Arg Leu Leu Ala Val Gly His Pro Tyr Phe Ser Ile Lys
            35                  40                  45

Arg Ala Asn Lys Thr Val Val Pro Lys Val Ser Gly Tyr Gln Tyr Arg
50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
            100                 105                 110

His Pro Phe Leu Asn Lys Tyr Asp Asp Val Glu Asn Ser Gly Ser Gly
            115                 120                 125

Gly Asn Pro Gly Gln Asp Asn Arg Val Asn Val Gly Met Asp Tyr Lys
130                 135                 140

Gln Thr Gln Leu Cys Met Val Gly Cys Ala Pro Pro Leu Gly Glu His
145                 150                 155                 160

Trp Gly Lys Gly Lys Gln Cys Thr Asn Thr Pro Val Gln Ala Gly Asp
                165                 170                 175

Cys Pro Pro Leu Glu Leu Ile Thr Ser Val Ile Gln Asp Gly Asp Met
            180                 185                 190

Val Asp Thr Gly Phe Gly Ala Met Asn Phe Ala Asp Leu Gln Thr Asn
            195                 200                 205

Lys Ser Asp Val Pro Ile Asp Ile Cys Gly Thr Thr Cys Lys Tyr Pro
210                 215                 220

Asp Tyr Leu Gln Met Ala Ala Asp Pro Tyr Gly Asp Arg Leu Phe Phe
225                 230                 235                 240

Phe Leu Arg Lys Glu Gln Met Phe Ala Arg His Phe Phe Asn Arg Ala
                245                 250                 255

Gly Glu Val Gly Glu Pro Val Pro Asp Thr Leu Ile Ile Lys Gly Ser
            260                 265                 270

Gly Asn Arg Thr Ser Val Gly Ser Ser Ile Tyr Val Asn Thr Pro Ser
            275                 280                 285

Gly Ser Leu Val Ser Ser Glu Ala Gln Leu Phe Asn Lys Pro Tyr Trp
290                 295                 300

Leu Gln Lys Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
                325                 330                 335

Cys Ala Ser Val Thr Thr Ser Ser Thr Tyr Thr Asn Ser Asp Tyr Lys
            340                 345                 350
```

```
Glu Tyr Met Arg His Val Glu Tyr Asp Leu Gln Phe Ile Phe Gln
        355                 360                 365
Leu Cys Ser Ile Thr Leu Ser Ala Glu Val Val Ala Tyr Ile His Thr
        370                 375                 380
Met Asn Pro Ser Val Leu Glu Asp Trp Asn Phe Gly Leu Ser Pro Pro
385                 390                 395                 400
Pro Asn Gly Thr Leu Glu Asp Thr Tyr Arg Tyr Val Gln Ser Gln Ala
                405                 410                 415
Ile Thr Cys Gln Lys Pro Thr Pro Glu Lys Gln Lys Pro Asp Pro Tyr
            420                 425                 430
Lys Asn Leu Ser Phe Trp Glu Val Asn Leu Lys Glu Lys Phe Ser Ser
                435                 440                 445
Glu Leu Asp Gln Tyr Pro Leu Gly Arg Lys Phe Leu Leu Gln Ser Gly
        450                 455                 460
Tyr Arg Gly Arg Ser Ser Ile Arg Thr Gly Val Lys Arg Pro Ala Val
465                 470                 475                 480
Ser Lys Ala Ser Ala Ala Pro Lys Arg Lys Arg Ala Lys Thr Lys Arg
                485                 490                 495

<210> SEQ ID NO 5
<211> LENGTH: 498
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<223> OTHER INFORMATION: H11N4-6T1

<400> SEQUENCE: 5

Met Ser Asp Ser Thr Val Tyr Val Pro Pro Asn Pro Val Ser Lys
1               5                   10                  15
Val Val Ala Thr Asp Ala Tyr Val Lys Arg Thr Asn Ile Phe Tyr His
            20                  25                  30
Ala Ser Ser Arg Leu Leu Ala Val Gly His Pro Tyr Phe Ser Ile
        35                  40                  45
Lys Arg Ala Asn Lys Thr Val Val Pro Lys Val Ser Gly Tyr Gln Tyr
    50                  55                  60
Arg Val Phe Lys Val Val Leu Pro Asp Pro Asn Lys Phe Ala Leu Pro
65                  70                  75                  80
Asp Ser Ser Leu Phe Asp Pro Thr Thr Gln Arg Leu Val Trp Ala Cys
                85                  90                  95
Thr Gly Leu Glu Val Gly Arg Gly Gln Pro Leu Gly Val Gly Val Ser
            100                 105                 110
Gly His Pro Leu Leu Asn Lys Tyr Asp Asp Val Glu Asn Ser Gly Gly
        115                 120                 125
Tyr Gly Gly Asn Pro Gly Gln Asp Asn Arg Val Asn Val Gly Met Asp
    130                 135                 140
Tyr Lys Gln Thr Gln Leu Cys Met Val Gly Cys Ala Pro Pro Leu Gly
145                 150                 155                 160
Glu His Trp Gly Lys Gly Thr Gln Cys Ser Asn Thr Ser Val Gln Asn
                165                 170                 175
Gly Asp Cys Pro Pro Leu Glu Leu Ile Thr Ser Val Ile Gln Asp Gly
            180                 185                 190
Asp Met Val Asp Thr Gly Phe Gly Ala Met Asn Phe Ala Asp Leu Gln
        195                 200                 205
```

```
Thr Asn Lys Ser Asp Val Pro Leu Asp Ile Cys Gly Thr Val Cys Lys
    210                 215                 220

Tyr Pro Asp Tyr Leu Gln Met Ala Ala Asp Pro Tyr Gly Asp Arg Leu
225                 230                 235                 240

Phe Phe Tyr Leu Arg Lys Glu Gln Met Phe Ala Arg His Phe Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
        275                 280                 285

Pro Ser Gly Ser Leu Val Ser Ser Glu Ala Gln Leu Phe Asn Lys Pro
    290                 295                 300

Tyr Trp Leu Gln Lys Ala Gln Gly His Asn Asn Gly Ile Cys Trp Gly
305                 310                 315                 320

Asn His Leu Phe Val Thr Val Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
    370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys

<210> SEQ ID NO 6
<211> LENGTH: 497
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<223> OTHER INFORMATION: H11N4-6T2

<400> SEQUENCE: 6

Met Ser Asp Ser Thr Val Tyr Val Pro Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Ser Arg Leu Leu Ala Val Gly His Pro Tyr Tyr Ser Ile
        35                  40                  45
```

```
Lys Lys Val Asn Lys Thr Val Val Pro Lys Val Ser Gly Tyr Gln Tyr
 50                  55                  60

Arg Val Phe Lys Val Val Leu Pro Asp Pro Asn Lys Phe Ala Leu Pro
 65                  70                  75                  80

Asp Ser Ser Leu Phe Asp Pro Thr Thr Gln Arg Leu Val Trp Ala Cys
                 85                  90                  95

Thr Gly Leu Glu Val Gly Arg Gly Gln Pro Leu Gly Val Gly Val Ser
            100                 105                 110

Gly His Pro Phe Leu Asn Lys Tyr Asp Asp Val Glu Asn Ser Gly Ser
        115                 120                 125

Gly Gly Asn Pro Gly Gln Asp Asn Arg Val Asn Val Gly Met Asp Tyr
    130                 135                 140

Lys Gln Thr Gln Leu Cys Met Val Gly Cys Ala Pro Pro Leu Gly Glu
145                 150                 155                 160

His Trp Gly Lys Gly Thr Gln Cys Ser Asn Thr Ser Val Gln Asn Gly
                165                 170                 175

Asp Cys Pro Pro Leu Glu Leu Ile Thr Ser Val Ile Gln Asp Gly Asp
            180                 185                 190

Met Val Asp Thr Gly Phe Gly Ala Met Asn Phe Ala Asp Leu Gln Thr
        195                 200                 205

Asn Lys Ser Asp Val Pro Leu Asp Ile Cys Gly Thr Val Cys Lys Tyr
    210                 215                 220

Pro Asp Tyr Leu Gln Met Ala Ala Asp Pro Tyr Gly Asp Arg Leu Phe
225                 230                 235                 240

Phe Tyr Leu Arg Lys Glu Gln Met Phe Ala Arg His Phe Phe Asn Arg
                245                 250                 255

Ala Gly Thr Val Gly Glu Pro Val Pro Asp Asp Leu Leu Val Lys Gly
            260                 265                 270

Gly Asn Asn Arg Ser Ser Val Ala Ser Ser Ile Tyr Val His Thr Pro
        275                 280                 285

Ser Gly Ser Leu Val Ser Ser Glu Ala Gln Leu Phe Asn Lys Pro Tyr
    290                 295                 300

Trp Leu Gln Lys Ala Gln Gly His Asn Asn Gly Ile Cys Trp Gly Asn
305                 310                 315                 320

His Leu Phe Val Thr Val Val Asp Thr Thr Arg Ser Thr Asn Met Thr
                325                 330                 335

Leu Cys Ala Ser Val Ser Lys Ser Ala Thr Tyr Thr Asn Ser Asp Tyr
            340                 345                 350

Lys Glu Tyr Met Arg His Val Glu Glu Phe Asp Leu Gln Phe Ile Phe
        355                 360                 365

Gln Leu Cys Ser Ile Thr Leu Ser Ala Glu Val Met Ala Tyr Ile His
    370                 375                 380

Thr Met Asn Pro Ser Val Leu Glu Asp Trp Asn Phe Gly Leu Ser Pro
385                 390                 395                 400

Pro Pro Asn Gly Thr Leu Glu Asp Thr Tyr Arg Tyr Val Gln Ser Gln
                405                 410                 415

Ala Ile Thr Cys Gln Lys Pro Thr Pro Glu Lys Glu Lys Gln Asp Pro
            420                 425                 430

Tyr Lys Asp Met Ser Phe Trp Glu Val Asn Leu Lys Glu Lys Phe Ser
        435                 440                 445

Ser Glu Leu Asp Gln Phe Pro Leu Gly Arg Lys Phe Leu Leu Gln Ser
    450                 455                 460

Gly Tyr Arg Gly Arg Thr Ser Ala Arg Thr Gly Ile Lys Arg Pro Ala
```

```
                465                 470                 475                 480
Val Ser Lys Pro Ser Thr Ala Pro Lys Arg Lys Arg Thr Lys Thr Lys
                    485                 490                 495

Lys

<210> SEQ ID NO 7
<211> LENGTH: 498
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<223> OTHER INFORMATION: H11N4-6T3

<400> SEQUENCE: 7

Met Ser Asp Ser Thr Val Tyr Val Pro Pro Asn Pro Val Ser Lys
1               5                   10                  15

Val Val Ala Thr Asp Ala Tyr Val Lys Arg Thr Asn Ile Phe Tyr His
                20                  25                  30

Ala Ser Ser Arg Leu Leu Ala Val Gly His Pro Tyr Tyr Ser Ile
            35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
                100                 105                 110

Gly His Pro Leu Leu Asn Lys Tyr Asp Asp Val Glu Asn Ser Gly Gly
            115                 120                 125

Tyr Gly Gly Asn Pro Gly Gln Asp Asn Arg Val Asn Val Gly Met Asp
    130                 135                 140

Tyr Lys Gln Thr Gln Leu Cys Met Val Gly Cys Ala Pro Pro Leu Gly
145                 150                 155                 160

Glu His Trp Gly Lys Gly Lys Gln Cys Thr Asn Thr Pro Val Gln Ala
                165                 170                 175

Gly Asp Cys Pro Pro Leu Glu Leu Ile Thr Ser Val Ile Gln Asp Gly
            180                 185                 190

Asp Met Val Asp Thr Gly Phe Gly Ala Met Asn Phe Ala Asp Leu Gln
    195                 200                 205

Thr Asn Lys Ser Asp Val Pro Leu Asp Ile Cys Gly Thr Val Cys Lys
210                 215                 220

Tyr Pro Asp Tyr Leu Gln Met Ala Ala Asp Pro Tyr Gly Asp Arg Leu
                225                 230                 235                 240

Phe Phe Tyr Leu Arg Lys Glu Gln Met Phe Ala Arg His Phe Asn
                245                 250                 255

Arg Ala Gly Thr Val Gly Glu Pro Val Pro Asp Asp Leu Leu Val Lys
            260                 265                 270

Gly Gly Asn Asn Arg Ser Ser Val Ala Ser Ser Ile Tyr Val His Thr
    275                 280                 285

Pro Ser Gly Ser Leu Val Ser Ser Glu Ala Gln Leu Phe Asn Lys Pro
290                 295                 300

Tyr Trp Leu Gln Lys Ala Gln Gly His Asn Asn Gly Ile Cys Trp Gly
305                 310                 315                 320
```

```
Asn His Leu Phe Val Thr Val Asp Thr Thr Arg Ser Thr Asn Met
                325                 330                 335

Thr Leu Cys Ala Ser Val Ser Lys Ser Ala Thr Tyr Thr Asn Ser Asp
            340                 345                 350

Tyr Lys Glu Tyr Met Arg His Val Glu Glu Phe Asp Leu Gln Phe Ile
        355                 360                 365

Phe Gln Leu Cys Ser Ile Thr Leu Ser Ala Glu Val Met Ala Tyr Ile
370                 375                 380

His Thr Met Asn Pro Ser Val Leu Glu Asp Trp Asn Phe Gly Leu Ser
385                 390                 395                 400

Pro Pro Pro Asn Gly Thr Leu Glu Asp Thr Tyr Arg Tyr Val Gln Ser
                405                 410                 415

Gln Ala Ile Thr Cys Gln Lys Pro Thr Pro Glu Lys Glu Lys Gln Asp
            420                 425                 430

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys

<210> SEQ ID NO 8
<211> LENGTH: 498
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<223> OTHER INFORMATION: H11N4-6T4

<400> SEQUENCE: 8

Met Ser Asp Ser Thr Val Tyr Val Pro Pro Asn Pro Val Ser Lys
1               5                   10                  15

Val Val Ala Thr Asp Ala Tyr Val Lys Arg Thr Asn Ile Phe Tyr His
            20                  25                  30

Ala Ser Ser Ser Arg Leu Leu Ala Val Gly His Pro Tyr Tyr Ser Ile
        35                  40                  45

Lys Lys Val Asn Lys Thr Val Val Pro Lys Val Ser Gly Tyr Gln Tyr
    50                  55                  60

Arg Val Phe Lys Val Val Leu Pro Asp Pro Asn Lys Phe Ala Leu Pro
65                  70                  75                  80

Asp Ser Ser Leu Phe Asp Pro Thr Thr Gln Arg Leu Val Trp Ala Cys
                85                  90                  95

Thr Gly Leu Glu Val Gly Arg Gly Gln Pro Leu Gly Val Gly Val Ser
            100                 105                 110

Gly His Pro Leu Leu Asn Lys Tyr Asp Asp Val Glu Asn Ser Gly Gly
        115                 120                 125

Tyr Gly Gly Asn Pro Gly Gln Asp Asn Arg Val Asn Val Gly Met Asp
    130                 135                 140

Tyr Lys Gln Thr Gln Leu Cys Met Val Gly Cys Ala Pro Pro Leu Gly
145                 150                 155                 160
```

```
Glu His Trp Gly Lys Gly Thr Gln Cys Ser Asn Thr Ser Val Gln Asn
                165                 170                 175
Gly Asp Cys Pro Pro Leu Glu Leu Ile Thr Ser Val Ile Gln Asp Gly
            180                 185                 190
Asp Met Val Asp Thr Gly Phe Gly Ala Met Asn Phe Ala Asp Leu Gln
        195                 200                 205
Thr Asn Lys Ser Asp Val Pro Leu Asp Ile Cys Gly Thr Val Cys Lys
    210                 215                 220
Tyr Pro Asp Tyr Leu Gln Met Ala Ala Asp Pro Tyr Gly Asp Arg Leu
225                 230                 235                 240
Phe Phe Tyr Leu Arg Lys Glu Gln Met Phe Ala Arg His Phe Phe Asn
                245                 250                 255
Arg Ala Gly Glu Val Gly Glu Pro Val Pro Asp Thr Leu Ile Ile Lys
            260                 265                 270
Gly Ser Gly Asn Arg Thr Ser Val Gly Ser Ser Ile Tyr Val His Thr
        275                 280                 285
Pro Ser Gly Ser Leu Val Ser Ser Glu Ala Gln Leu Phe Asn Lys Pro
    290                 295                 300
Tyr Trp Leu Gln Lys Ala Gln Gly His Asn Asn Gly Ile Cys Trp Gly
305                 310                 315                 320
Asn His Leu Phe Val Thr Val Val Asp Thr Thr Arg Ser Thr Asn Met
                325                 330                 335
Thr Leu Cys Ala Ser Val Ser Lys Ser Ala Thr Tyr Thr Asn Ser Asp
            340                 345                 350
Tyr Lys Glu Tyr Met Arg His Val Glu Glu Phe Asp Leu Gln Phe Ile
        355                 360                 365
Phe Gln Leu Cys Ser Ile Thr Leu Ser Ala Glu Val Met Ala Tyr Ile
    370                 375                 380
His Thr Met Asn Pro Ser Val Leu Glu Asp Trp Asn Phe Gly Leu Ser
385                 390                 395                 400
Pro Pro Pro Asn Gly Thr Leu Glu Asp Thr Tyr Arg Tyr Val Gln Ser
                405                 410                 415
Gln Ala Ile Thr Cys Gln Lys Pro Thr Pro Glu Lys Glu Lys Gln Asp
            420                 425                 430
Pro Tyr Lys Asp Met Ser Phe Trp Glu Val Asn Leu Lys Glu Lys Phe
        435                 440                 445
Ser Ser Glu Leu Asp Gln Phe Pro Leu Gly Arg Lys Phe Leu Leu Gln
    450                 455                 460
Ser Gly Tyr Arg Gly Arg Thr Ser Ala Arg Thr Gly Ile Lys Arg Pro
465                 470                 475                 480
Ala Val Ser Lys Pro Ser Thr Ala Pro Lys Arg Lys Arg Thr Lys Thr
                485                 490                 495
Lys Lys

<210> SEQ ID NO 9
<211> LENGTH: 498
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<223> OTHER INFORMATION: H11N4-6T5

<400> SEQUENCE: 9

Met Ser Asp Ser Thr Val Tyr Val Pro Pro Pro Asn Pro Val Ser Lys
```

```
              1               5                  10                 15
Val Val Ala Thr Asp Ala Tyr Val Lys Arg Thr Asn Ile Phe Tyr His
              20                 25                 30
Ala Ser Ser Ser Arg Leu Leu Ala Val Gly His Pro Tyr Tyr Ser Ile
              35                 40                 45
Lys Lys Val Asn Lys Thr Val Val Pro Lys Val Ser Gly Tyr Gln Tyr
              50                 55                 60
Arg Val Phe Lys Val Val Leu Pro Asp Pro Asn Lys Phe Ala Leu Pro
65                     70                 75                 80
Asp Ser Ser Leu Phe Asp Pro Thr Thr Gln Arg Leu Val Trp Ala Cys
                  85                 90                 95
Thr Gly Leu Glu Val Gly Arg Gly Gln Pro Leu Gly Val Gly Val Ser
                  100                105                110
Gly His Pro Leu Leu Asn Lys Tyr Asp Asp Val Glu Asn Ser Gly Gly
                  115                120                125
Tyr Gly Gly Asn Pro Gly Gln Asp Asn Arg Val Asn Val Gly Met Asp
                  130                135                140
Tyr Lys Gln Thr Gln Leu Cys Met Val Gly Cys Ala Pro Pro Leu Gly
145                    150                155                160
Glu His Trp Gly Lys Gly Thr Gln Cys Ser Asn Thr Ser Val Gln Asn
                  165                170                175
Gly Asp Cys Pro Pro Leu Glu Leu Ile Thr Ser Val Ile Gln Asp Gly
                  180                185                190
Asp Met Val Asp Thr Gly Phe Gly Ala Met Asn Phe Ala Asp Leu Gln
                  195                200                205
Thr Asn Lys Ser Asp Val Pro Leu Asp Ile Cys Gly Thr Val Cys Lys
                  210                215                220
Tyr Pro Asp Tyr Leu Gln Met Ala Ala Asp Pro Tyr Gly Asp Arg Leu
225                    230                235                240
Phe Phe Tyr Leu Arg Lys Glu Gln Met Phe Ala Arg His Phe Phe Asn
                  245                250                255
Arg Ala Gly Thr Val Gly Glu Pro Val Pro Asp Asp Leu Leu Val Lys
                  260                265                270
Gly Gly Asn Asn Arg Ser Ser Val Ala Ser Ser Ile Tyr Val His Thr
                  275                280                285
Pro Ser Gly Ser Leu Val Ser Ser Glu Ala Gln Leu Phe Asn Lys Pro
                  290                295                300
Tyr Trp Leu Gln Lys Ala Gln Gly His Asn Asn Gly Ile Cys Trp Gly
305                    310                315                320
Asn His Leu Phe Val Thr Val Val Asp Thr Thr Arg Ser Thr Asn Met
                  325                330                335
Thr Leu Cys Ala Ser Val Thr Thr Ser Ser Thr Tyr Thr Asn Ser Asp
                  340                345                350
Tyr Lys Glu Tyr Met Arg His Val Glu Glu Phe Asp Leu Gln Phe Ile
                  355                360                365
Phe Gln Leu Cys Ser Ile Thr Leu Ser Ala Glu Val Met Ala Tyr Ile
                  370                375                380
His Thr Met Asn Pro Ser Val Leu Glu Asp Trp Asn Phe Gly Leu Ser
385                    390                395                400
Pro Pro Pro Asn Gly Thr Leu Glu Asp Thr Tyr Arg Tyr Val Gln Ser
                  405                410                415
Gln Ala Ile Thr Cys Gln Lys Pro Thr Pro Glu Lys Glu Lys Gln Asp
                  420                425                430
```

Pro Tyr Lys Asp Met Ser Phe Trp Glu Val Asn Leu Lys Glu Lys Phe
        435                 440                 445

Ser Ser Glu Leu Asp Gln Phe Pro Leu Gly Arg Lys Phe Leu Leu Gln
    450                 455                 460

Ser Gly Tyr Arg Gly Arg Thr Ser Ala Arg Thr Gly Ile Lys Arg Pro
465                 470                 475                 480

Ala Val Ser Lys Pro Ser Thr Ala Pro Lys Arg Lys Arg Thr Lys Thr
                485                 490                 495

Lys Lys

<210> SEQ ID NO 10
<211> LENGTH: 1497
<212> TYPE: DNA
<213> ORGANISM: Artificial Sequence
<220> FEATURE:
<223> OTHER INFORMATION: HPV11N4

<400> SEQUENCE: 10

| | | |
|---|---|---|
| atgagcgaca gcacagtata tgtgcctcct cccaaccctg tatccaaggt tgttgccacg | 60 |
| gatgcgtatg ttaaacgcac caacatattt tatcacgcca gcagttctag actccttgct | 120 |
| gtgggacatc catattactc tatcaaaaaa gttaacaaaa cagttgtacc aaaggtgtct | 180 |
| ggatatcaat atagagtgtt taaggtagtg ttgccagatc ctaacaagtt tgcattacct | 240 |
| gattcatctc tgtttgaccc cactacacag cgtttagtat gggcgtgcac agggttggag | 300 |
| gtaggcaggg gtcaaccttt aggcgttggt gttagtgggc atccattgct aaacaaatat | 360 |
| gatgatgtag aaaatagtgg tgggtatggt ggtaatcctg gtcaggataa tagggttaat | 420 |
| gtaggtatgg attataaaca aacccagcta tgtatggtgg gctgtgctcc accgttaggt | 480 |
| gaacattggg gtaagggtac acaatgttca ataccctctg tacaaaatgg tgactgcccc | 540 |
| ccgttggaac ttattaccag tgttatacag gatggggaca tggttgatac aggctttggt | 600 |
| gctatgaatt ttgcagactt acaaaccaat aaatcggatg ttccccttga tatttgtgga | 660 |
| actgtctgca aatatcctga ttatttgcaa atggcagcag accctatgg tgataggttg | 720 |
| ttttttttatt tgcgaaagga acaaatgttt gctagacact tttttaatag ggccggtact | 780 |
| gtggggggaac ctgtgcctga tgacctgttg gtaaaagggg gtaataatag gtcatctgta | 840 |
| gctagtagta tttatgtaca tacacctagt ggatccttgg tgtcttcaga ggctcaatta | 900 |
| tttaataaac catattggct tcaaaaggct cagggacata acaatggtat ttgctgggga | 960 |
| aaccacttgt ttgttactgt ggtagatacc acacgcagta caaatatgac actatgtgca | 1020 |
| tctgtgtcta aatctgctac atacactaat tcagattata aggaatatat gcgccatgtg | 1080 |
| gaggagtttg atttacagtt tattttttcaa ttgtgtagca ttacattatc tgcagaagtc | 1140 |
| atggcctata tacacacaat gaatccttct gttttggagg actggaactt tggtttatcg | 1200 |
| cctccaccaa atggtacact ggaggatact tatagatatg tacagtcaca ggccattacc | 1260 |
| tgtcagaaac ccacacccga aaagaaaaa caggacccct ataaggatat gagtttttgg | 1320 |
| gaggttaact aaaagaaaaa gttttcttct gaattagatc agtttcccct tggacgtaag | 1380 |
| ttttttattgc aaagtggata tcgaggacgg acgtctgctc gtacaggtat aaagcgccca | 1440 |
| gctgtgtcta agccctctac agcccccaaa cgaaaacgta ccaaaaccaa aaagtaa | 1497 |

<210> SEQ ID NO 11
<211> LENGTH: 1491
<212> TYPE: DNA

<213> ORGANISM: Artificial Sequence
<220> FEATURE:
<223> OTHER INFORMATION: HPV6N5

<400> SEQUENCE: 11

| | | | | | |
|---|---|---|---|---|---|
| atggacagca | cagtatatgt | gcctcctcct | aaccctgtat | ccaaagttgt | tgccacggat | 60 |
| gcttatgtta | ctcgcaccaa | catattttat | catgccagca | gttctagact | tcttgcagtg | 120 |
| ggtcatcctt | atttttccat | aaaacgggct | aacaaaactg | ttgtgccaaa | ggtgtcagga | 180 |
| tatcaataca | gggtatttaa | ggtggtgtta | ccagatccta | acaaatttgc | attgcctgac | 240 |
| tcgtctcttt | ttgatcccac | aacacaacgt | ttggtatggg | catgcacagg | cctagaggtg | 300 |
| ggcaggggac | agccattagg | tgtgggtgta | agtggacatc | ctttcctaaa | taaatatgat | 360 |
| gatgttgaaa | attcagggag | tggtggtaac | cctggacagg | ataacagggt | taatgttggt | 420 |
| atggattata | acaaacaca | attatgcatg | gttggatgtg | ccccccttt | gggcgagcat | 480 |
| tggggtaaag | gtaaacagtg | tactaataca | cctgtacagg | ctggtgactg | cccgccctta | 540 |
| gaacttatta | ccagtgttat | acaggatggc | gatatggttg | acacaggctt | tggtgctatg | 600 |
| aattttgctg | atttgcagac | caataaatca | gatgttccta | ttgatatatg | tggcactaca | 660 |
| tgtaaatatc | cagattattt | acaaatggct | gcagacccttt | atggtgatag | attattttt | 720 |
| tttctacgga | aggaacaaat | gtttgccaga | catttttta | acagggctgg | cgaggtgggg | 780 |
| gaacctgtgc | ctgatactct | tataattaag | ggtagtggaa | atcgaacgtc | tgtagggagt | 840 |
| agtatatatg | ttaacacccc | aagcggctct | ttggtgtcct | ctgaggcaca | attgtttaat | 900 |
| aagccatatt | ggctacaaaa | agcccaggga | cataacaatg | gtatttgttg | gggtaatcaa | 960 |
| ctgtttgtta | ctgtggtaga | taccacacgc | agtaccaaca | tgacattatg | tgcatccgta | 1020 |
| actacatctt | ccacatacac | caattctgat | tataaagagt | acatgcgtca | tgtggaagag | 1080 |
| tatgatttac | aatttatttt | tcaattatgt | agcattacat | tgtctgctga | agtagtggcc | 1140 |
| tatattcaca | caatgaatcc | ctctgttttg | gaagactgga | actttgggtt | atcgcctccc | 1200 |
| ccaaatggta | cattagaaga | tacctatagg | tatgtgcagt | cacaggccat | tacctgtcaa | 1260 |
| aagcccactc | ctgaaaagca | aaagccagat | ccctataaga | accttagttt | tggggaggtt | 1320 |
| aatttaaaag | aaaagtttc | tagtgaattg | gatcagtatc | ctttgggacg | caagttttg | 1380 |
| ttacaaagtg | gatatagggg | acggtcctct | attcgtaccg | tgttaagcg | ccctgctgtt | 1440 |
| tccaaagcct | ctgctgcccc | taaacgtaag | cgcgccaaaa | ctaaaaggta | a | 1491 |

<210> SEQ ID NO 12
<211> LENGTH: 1497
<212> TYPE: DNA
<213> ORGANISM: Artificial Sequence
<220> FEATURE:
<223> OTHER INFORMATION: H11N4-6T1

<400> SEQUENCE: 12

| | | | | | |
|---|---|---|---|---|---|
| atgagcgaca | gcacagtata | tgtgcctcct | cccaaccctg | tatccaaggt | tgttgccacg | 60 |
| gatgcgtatg | ttaaacgcac | caacatattt | tatcacgcca | gcagttctag | actccttgct | 120 |
| gtgggacatc | catatttttc | cataaaacgg | ctaacaaaa | ctgttgtgcc | aaaggtgtca | 180 |
| ggatatcaat | atagagtgtt | taaggtagtg | ttgccagatc | ctaacaagtt | tgcattacct | 240 |
| gattcatctc | tgtttgaccc | cactacacag | cgtttagtat | gggcgtgcac | agggttggag | 300 |
| gtaggcaggg | gtcaaccttt | aggcgttggt | gttagtgggc | atccattgct | aaacaaatat | 360 |
| gatgatgtag | aaaatagtgg | tgggtatggt | ggtaatcctg | gtcaggataa | tagggttaat | 420 |

```
gtaggtatgg attataaaca aacccagcta tgtatggtgg gctgtgctcc accgttaggt      480
gaacattggg gtaagggtac acaatgttca aatacctctg tacaaaatgg tgactgcccc      540
ccgttggaac ttattaccag tgttatacag gatggggaca tggttgatac aggctttggt      600
gctatgaatt ttgcagactt acaaaccaat aaatcggatg ttccccttga tatttgtgga      660
actgtctgca aatatcctga ttatttgcaa atggcagcag acccttatgg tgataggttg      720
tttttttatt tgcgaaagga acaaatgttt gctagacact ttttaatag ggccggtact       780 gtggggggaac ctgtgcctga tgacctgttg gtaaagggg gtaataatag gtcatctgta      840
gctagtagta tttatgtaca tacacctagt ggatccttgg tgtcttcaga ggctcaatta      900
tttaataaac catattggct tcaaaaggct cagggacata acaatggtat ttgctgggga      960
aaccacttgt tgttactgt ggtagatacc acacgcagta caaatatgac actatgtgca     1020
tctgtgtcta aatctgctac atacactaat tcagattata aggaatatat gcgccatgtg     1080
gaggagtttg atttacagtt tatttttcaa ttgtgtagca ttacattatc tgcagaagtc     1140
atggcctata tacacacaat gaatccttct gttttggagg actggaactt tggtttatcg     1200
cctccaccaa atggtacact ggaggatact tatagatatg tacagtcaca ggccattacc     1260
tgtcagaaac ccacacccga aaagaaaaa caggacccct ataaggatat gagtttttgg      1320
gaggttaact taaaagaaaa gttttcttct gaattagatc agtttcccct tggacgtaag     1380
tttttattgc aaagtggata tcgaggacgg acgtctgctc gtacaggtat aaagcgccca     1440
gctgtgtcta agccctctac agcccccaaa cgaaaacgta ccaaaaccaa aaagtaa       1497
```

<210> SEQ ID NO 13
<211> LENGTH: 1494
<212> TYPE: DNA
<213> ORGANISM: Artificial Sequence
<220> FEATURE:
<223> OTHER INFORMATION: H11N4-6T2

<400> SEQUENCE: 13

```
atgagcgaca gcacagtata tgtgcctcct cccaaccctg tatccaaggt tgttgccacg       60
gatgcgtatg ttaaacgcac caacatattt tatcacgcca gcagttctag actccttgct     120
gtgggacatc catattactc tatcaaaaaa gttaacaaaa cagttgtacc aaaggtgtct     180
ggatatcaat atagagtgtt taaggtagtg ttgccagatc ctaacaagtt tgcattacct     240
gattcatctc tgtttgaccc cactacacag cgtttagtat gggcgtgcac agggttggag     300
gtaggcaggg gacagccatt aggtgtgggt gtaagtggac atccttcct aaataaatat      360 gatgatgttg aaaattcagg gagtggtggt aaccctggac aggataacag ggttaatgtt     420
ggtatggatt ataaacaaac ccagctatgt atggtgggct gtgctccacc gttaggtgaa     480
cattggggta agggtacaca atgttcaaat acctctgtac aaaatggtga ctgcccccg      540 ttggaactta ttaccagtgt tatacaggat ggggacatgg ttgatacagg ctttggtgct     600
atgaattttg cagacttaca aaccaataaa tcggatgttc cccttgatat ttgtggaact     660
gtctgcaaat atcctgatta tttgcaaatg gcagcagacc cttatggtga taggttgttt     720
ttttatttgc gaaaggaaca aatgtttgct agacactttt taataggc cggtactgtg      780 ggggaacctg tgcctgatga cctgttggta aaggggta ataataggtc atctgtagct      840
agtagtattt atgtacatac acctagtgga tccttggtgt cttcagaggc tcaattattt     900
aataaaccat attggcttca aaaggctcag ggacataaca atggtatttg ctgggaaac      960
```

| | |
|---|---|
| cacttgtttg ttactgtggt agataccaca cgcagtacaa atatgacact atgtgcatct | 1020 |
| gtgtctaaat ctgctacata cactaattca gattataagg aatatatgcg ccatgtggag | 1080 |
| gagtttgatt tacagtttat ttttcaattg tgtagcatta cattatctgc agaagtcatg | 1140 |
| gcctatatac acacaatgaa tccttctgtt ttggaggact ggaactttgg tttatcgcct | 1200 |
| ccaccaaatg gtacactgga ggatacttat agatatgtac agtcacaggc cattacctgt | 1260 |
| cagaaaccca cacccgaaaa agaaaaacag gaccccctata aggatatgag tttttgggag | 1320 |
| gttaacttaa aagaaaagtt ttcttctgaa ttagatcagt ttccccttgg acgtaagttt | 1380 |
| ttattgcaaa gtggatatcg aggacggacg tctgctcgta caggtataaa gcgcccagct | 1440 |
| gtgtctaagc cctctacagc ccccaaacga aaacgtacca aaaccaaaaa gtaa | 1494 |

<210> SEQ ID NO 14
<211> LENGTH: 1497
<212> TYPE: DNA
<213> ORGANISM: Artificial Sequence
<220> FEATURE:
<223> OTHER INFORMATION: H11N4-6T3

<400> SEQUENCE: 14

| | |
|---|---|
| atgagcgaca gcacagtata tgtgcctcct cccaaccctg tatccaaggt tgttgccacg | 60 |
| gatgcgtatg ttaaacgcac caacatattt tatcacgcca gcagttctag actccttgct | 120 |
| gtgggacatc catattactc tatcaaaaaa gttaacaaaa cagttgtacc aaaggtgtct | 180 |
| ggatatcaat atagagtgtt taaggtagtg ttgccagatc ctaacaagtt tgcattacct | 240 |
| gattcatctc tgtttgaccc cactacacag cgtttagtat gggcgtgcac agggttggag | 300 |
| gtaggcaggg gtcaaccttt aggcgttggt gttagtgggc atccattgct aaacaaatat | 360 |
| gatgatgtag aaaatagtgg tgggtatggt ggtaatcctg gtcaggataa tagggttaat | 420 |
| gtaggtatgg attataaaca aacccagcta tgtatggtgg gctgtgctcc accgttaggt | 480 |
| gaacattggg gtaaaggtaa acagtgtact aatacacctg tacaggctgg tgactgcccg | 540 |
| cccttggaac ttattaccag tgttatacag gatggggaca tggttgatac aggctttggt | 600 |
| gctatgaatt ttgcagactt acaaaccaat aaatcggatg ttccccttga tatttgtgga | 660 |
| actgtctgca aatatcctga ttatttgcaa atggcagcag acccttatgg tgataggttg | 720 |
| ttttttttatt tgcgaaagga acaaatgttt gctagacact ttttaatag ggccggtact | 780 |
| gtgggggaac ctgtgcctga tgacctgttg gtaaagggg gtaataatag gtcatctgta | 840 |
| gctagtagta tttatgtaca tacacctagt ggatccttgg tgtcttcaga ggctcaatta | 900 |
| tttaataaac catattggct tcaaaaggct cagggacata acaatggtat ttgctgggga | 960 |
| aaccacttgt tgttactgt ggtagatacc acacgcagta caaatatgac actatgtgca | 1020 |
| tctgtgtcta atctgctac atacactaat tcagattata aggaatatat gcgccatgtg | 1080 |
| gaggagtttg atttacagtt tattttttcaa ttgtgtagca ttacattatc tgcagaagtc | 1140 |
| atggcctata cacacaat gaatccttct gttttggagg actggaactt ggtttatcg | 1200 |
| cctccaccaa atggtacact ggaggatact tatagatatg tacagtcaca ggccattacc | 1260 |
| tgtcagaaac ccacacccga aaagaaaaa caggacccct ataaggatat gagttttttgg | 1320 |
| gaggttaact aaaagaaaa gttttcttct gaattagatc agttttcccct ggacgtaag | 1380 |
| tttttattgc aaagtggata tcgaggacgg acgtctgctc gtacaggtat aaagcgccca | 1440 |
| gctgtgtcta agccctctac agcccccaaa cgaaaacgta ccaaaaccaa aaagtaa | 1497 |

<210> SEQ ID NO 15
<211> LENGTH: 1497
<212> TYPE: DNA
<213> ORGANISM: Artificial Sequence
<220> FEATURE:
<223> OTHER INFORMATION: H11N4-6T4

<400> SEQUENCE: 15

| | | | | | |
|---|---|---|---|---|---|
| atgagcgaca | gcacagtata | tgtgcctcct | cccaaccctg | tatccaaggt | tgttgccacg | 60 |
| gatgcgtatg | ttaaacgcac | caacatattt | tatcacgcca | gcagttctag | actccttgct | 120 |
| gtgggacatc | catattactc | tatcaaaaaa | gttaacaaaa | cagttgtacc | aaaggtgtct | 180 |
| ggatatcaat | atagagtgtt | taaggtagtg | ttgccagatc | ctaacaagtt | tgcattacct | 240 |
| gattcatctc | tgtttgaccc | cactacacag | cgtttagtat | gggcgtgcac | agggttggag | 300 |
| gtaggcaggg | gtcaaccttt | aggcgttggt | gttagtgggc | atccattgct | aaacaaatat | 360 |
| gatgatgtag | aaaatagtgg | tgggtatggt | ggtaatcctg | gtcaggataa | tagggttaat | 420 |
| gtaggtatgg | attataaaca | aacccagcta | tgtatggtgg | gctgtgctcc | accgttaggt | 480 |
| gaacattggg | gtaagggtac | acaatgttca | aatacctctg | tacaaaatgg | tgactgcccc | 540 |
| ccgttggaac | ttattaccag | tgttatacag | gatggggaca | tggttgatac | aggctttggt | 600 |
| gctatgaatt | ttgcagactt | acaaaccaat | aaatcggatg | ttccccttga | tatttgtgga | 660 |
| actgtctgca | aatatcctga | ttatttgcaa | atggcagcag | accctatgg | tgataggttg | 720 |
| ttttttatt | tgcgaaagga | acaaatgttt | gctagacact | tttttaacag | ggctggcgag | 780 |
| gtggggaac | ctgtgcctga | tactcttata | attaagggta | gtggaaatcg | aacgtctgta | 840 |
| gggagtagta | tatatgtaca | tacacctagt | ggatccttgg | tgtcttcaga | ggctcaatta | 900 |
| tttaataaac | catattggct | tcaaaaggct | cagggacata | caatggtat | ttgctgggga | 960 |
| aaccacttgt | tgttactgt | ggtagatacc | acacgcagta | caaatatgac | actatgtgca | 1020 |
| tctgtgtcta | aatctgctac | atacactaat | tcagattata | aggaatatat | gcgccatgtg | 1080 |
| gaggagtttg | atttacagtt | tattttcaa | ttgtgtagca | ttacattatc | tgcagaagtc | 1140 |
| atggcctata | tacacacaat | gaatccttct | gttttggagg | actggaactt | tggtttatcg | 1200 |
| cctccaccaa | atggtacact | ggaggatact | tatagatatg | tacagtcaca | ggccattacc | 1260 |
| tgtcagaaac | ccacacccga | aaagaaaaa | caggacccct | ataaggatat | gagttttgg | 1320 |
| gaggttaact | taaagaaaa | gttttcttct | gaattagatc | agtttcccct | tggacgtaag | 1380 |
| tttttattgc | aaagtggata | tcgaggacgg | acgtctgctc | gtacaggtat | aaagcgccca | 1440 |
| gctgtgtcta | agccctctac | agcccccaaa | cgaaaacgta | ccaaaaccaa | aaagtaa | 1497 |

<210> SEQ ID NO 16
<211> LENGTH: 1497
<212> TYPE: DNA
<213> ORGANISM: Artificial Sequence
<220> FEATURE:
<223> OTHER INFORMATION: H11N4-6T5

<400> SEQUENCE: 16

| | | | | | |
|---|---|---|---|---|---|
| atgagcgaca | gcacagtata | tgtgcctcct | cccaaccctg | tatccaaggt | tgttgccacg | 60 |
| gatgcgtatg | ttaaacgcac | caacatattt | tatcacgcca | gcagttctag | actccttgct | 120 |
| gtgggacatc | catattactc | tatcaaaaaa | gttaacaaaa | cagttgtacc | aaaggtgtct | 180 |
| ggatatcaat | atagagtgtt | taaggtagtg | ttgccagatc | ctaacaagtt | tgcattacct | 240 |
| gattcatctc | tgtttgaccc | cactacacag | cgtttagtat | gggcgtgcac | agggttggag | 300 |

```
gtaggcaggg gtcaacctttt aggcgttggt gttagtgggc atccattgct aaacaaatat    360
gatgatgtag aaaatagtgg tgggtatggt ggtaatcctg gtcaggataa tagggttaat    420
gtaggtatgg attataaaca aacccagcta tgtatggtgg gctgtgctcc accgttaggt    480
gaacattggg gtaagggtac acaatgttca aatacctctg tacaaaatgg tgactgcccc    540
ccgttggaac ttattaccag tgttatacag gatggggaca tggttgatac aggctttggt    600
gctatgaatt ttgcagactt acaaaccaat aaatcggatg ttccccttga tatttgtgga    660
actgtctgca aatatcctga ttatttgcaa atggcagcag acccttatgg tgataggttg    720 ttttttttatt tgcgaaagga acaaatgttt gctagacact tttttaatag ggccggtact    780 gtggggaac ctgtgcctga tgacctgttg gtaaagggg gtaataatag gtcatctgta    840
gctagtagta tttatgtaca tacacctagt ggatccttgg tgtcttcaga ggctcaatta    900
tttaataaac catattggct tcaaaaggct cagggacata acaatggtat ttgctgggga    960
aaccacttgt tgttactgt ggtagatacc acacgcagta caaatatgac actatgtgca   1020
tctgtaacta catcttccac atacaccaat tctgattata aggaatatat gcgccatgtg   1080
gaggagtttg atttacagtt tattttttcaa ttgtgtagca ttacattatc tgcagaagtc   1140
atggcctata tacacacaat gaatccttct gttttggagg actggaactt tggtttatcg   1200
cctccaccaa atggtacact ggaggatact tatagatatg tacagtcaca ggccattacc   1260
tgtcagaaac ccacacccga aaagaaaaa caggacccct ataaggatat gagttttttgg   1320 gaggttaact aaaagaaaa gttttcttct gaattagatc agtttcccct tggacgtaag   1380
tttttattgc aaagtggata tcgaggacgg acgtctgctc gtacaggtat aaagcgccca   1440
gctgtgtcta gccctctac agcccccaaa cgaaaacgta ccaaaccaa aaagtaa   1497

<210> SEQ ID NO 17
<211> LENGTH: 49
<212> TYPE: DNA
<213> ORGANISM: Artificial Sequence
<220> FEATURE:
<223> OTHER INFORMATION: primer

<400> SEQUENCE: 17
gtgggacatc catattttc tatcaaacgg gctaacaaaa cagttgtac                 49

<210> SEQ ID NO 18
<211> LENGTH: 49
<212> TYPE: DNA
<213> ORGANISM: Artificial Sequence
<220> FEATURE:
<223> OTHER INFORMATION: primer

<400> SEQUENCE: 18
gtacaactgt tttgttagcc cgtttgatag aaaaatatgg atgtcccac                 49

<210> SEQ ID NO 19
<211> LENGTH: 48
<212> TYPE: DNA
<213> ORGANISM: Artificial Sequence
<220> FEATURE:
<223> OTHER INFORMATION: primer

<400> SEQUENCE: 19
tcaatataga gtgtttaagg tagtgttacc agatcctaac aaatttgc                  48

<210> SEQ ID NO 20
<211> LENGTH: 43
```

```
<212> TYPE: DNA
<213> ORGANISM: Artificial Sequence
<220> FEATURE:
<223> OTHER INFORMATION: primer

<400> SEQUENCE: 20
cccaccatac atagctgggt ttgtttataa tccataccaa cat         43

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
aaacaaaccc agctatgtat ggtgg                             25

<210> SEQ ID NO 22
<211> LENGTH: 26
<212> TYPE: DNA
<213> ORGANISM: Artificial Sequence
<220> FEATURE:
<223> OTHER INFORMATION: primer

<400> SEQUENCE: 22
cactacctta aacactctat attgat                            26

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
ctgtacagaa tggtgactgc ccgcccttag                        30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
aacactgtgt acctttaccc caatgctcgc                        30

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
taatacatct gtacagaatg gtgactgccc gcccttag               38

<210> SEQ ID NO 26
<211> LENGTH: 39
<212> TYPE: DNA
<213> ORGANISM: Artificial Sequence
<220> FEATURE:
<223> OTHER INFORMATION: primer

<400> SEQUENCE: 26
```
gatgtattag aacactgtgt acctttaccc caatgctcg        39

<210> SEQ ID NO 27
<211> LENGTH: 47
<212> TYPE: DNA
<213> ORGANISM: Artificial Sequence
<220> FEATURE:
<223> OTHER INFORMATION: primer

<400> SEQUENCE: 27
ggaacaaatg tttgctagac acttttttaa cagggctggc gaggtgg        47

<210> SEQ ID NO 28
<211> LENGTH: 46
<212> TYPE: DNA
<213> ORGANISM: Artificial Sequence
<220> FEATURE:
<223> OTHER INFORMATION: primer

<400> SEQUENCE: 28
accaaggatc cactaggtgt atgaacatat atactactcc ctacag        46

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
catacaccta gtggatcctt gg        22

<210> SEQ ID NO 30
<211> LENGTH: 26
<212> TYPE: DNA
<213> ORGANISM: Artificial Sequence
<220> FEATURE:
<223> OTHER INFORMATION: primer

<400> SEQUENCE: 30
aaagtgtcta gcaaacattt gttcct        26

<210> SEQ ID NO 31
<211> LENGTH: 45
<212> TYPE: DNA
<213> ORGANISM: Artificial Sequence
<220> FEATURE:
<223> OTHER INFORMATION: primer

<400> SEQUENCE: 31
tggtatttgc tggggaaacc acctgtttgt tactgtggta gatac        45

<210> SEQ ID NO 32
<211> LENGTH: 46
<212> TYPE: DNA
<213> ORGANISM: Artificial Sequence
<220> FEATURE:
<223> OTHER INFORMATION: primer

<400> SEQUENCE: 32
gaaaaataaa ctgtaaatca aactcttcca catgacgcat gtactc        46

<210> SEQ ID NO 33
<211> LENGTH: 22
<212> TYPE: DNA
<213> ORGANISM: Artificial Sequence

```
<220> FEATURE:
<223> OTHER INFORMATION: primer

<400> SEQUENCE: 33
tttgatttac agtttatttt tc                                              22

<210> SEQ ID NO 34
<211> LENGTH: 25
<212> TYPE: DNA
<213> ORGANISM: Artificial Sequence
<220> FEATURE:
<223> OTHER INFORMATION: primer

<400> SEQUENCE: 34
gtggtttccc cagcaaatac cattg                                           25

<210> SEQ ID NO 35
<211> LENGTH: 10
<212> TYPE: PRT
<213> ORGANISM: Artificial Sequence
<220> FEATURE:
<223> OTHER INFORMATION: HPV6

<400> SEQUENCE: 35

Lys Gln Cys Thr Asn Thr Pro Val Gln Ala
1               5                   10

<210> SEQ ID NO 36
<211> LENGTH: 6
<212> TYPE: PRT
<213> ORGANISM: Artificial Sequence
<220> FEATURE:
<223> OTHER INFORMATION: HPV6

<400> SEQUENCE: 36

Thr Thr Ser Ser Thr Tyr
1               5

<210> SEQ ID NO 37
<211> LENGTH: 21
<212> TYPE: PRT
<213> ORGANISM: Artificial Sequence
<220> FEATURE:
<223> OTHER INFORMATION: HPV6

<400> SEQUENCE: 37

Phe Leu Asn Lys Tyr Asp Asp Val Glu Asn Ser Gly Ser Gly Gly Asn
1               5                   10                  15

Pro Gly Gln Asp Asn
            20
```

MUTANT OF L1 PROTEIN OF HUMAN PAPILLOMAVIRUS TYPE 11

CROSS-REFERENCE TO RELATED APPLICATIONS

This application is National Stage Application and claims priority under 35 U.S.C. § 371 to Patent Cooperation Treaty application PCT/CN2016/108349, filed Dec. 2, 2016, which claims the benefit of Chinese Patent Application No. 201510887801.9, filed Dec. 4, 2015, priory is claimed to both of these applications and the disclosures of these prior applications are considered part of the disclosure of this application and to the extent allowed the entire contents of the aforementioned applications are incorporated herein.

SEQUENCE LISTING

This application incorporates in its entirety the Sequence Listing entitled "2018-06-04 235427-433902-Sequence_Listing_ST25.txt" (57,876 bytes), which was created on Jun. 4, 2018 and filed electronically herewith.

TECHNICAL FIELD

The invention relates to the field of molecular virology and immunology. In particular, the invention relates to a mutated HPV11 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV11 and HPV6), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

BACKGROUND ART

Human Papillomavirus (HPV) mainly causes warts in skin and mucosa. HPV types are divided into high-risk types and low-risk types depending on their association with tumorigenesis. Among them, infection by high-risk HPV types has been demonstrated to be the leading cause of genital cancer including cervical cancer in women; and low-risk HPV types mainly cause condyloma acuminatum. The most effective way to prevent and control HPV infection is to vaccinate HPV vaccines, particularly vaccines against high-risk HPV types causing cervical cancer.

Major capsid protein L1 of HPV has the characteristic of self-assembling into hollow Virus-Like Particle (VLP). HPV VLP has a symmetrical icosahedral structure composed of 72 pentamers of major capsid protein L1 (Doorbar, J. and P. H. Gallimore. 1987. J Virol, 61(9): 2793-9). HPV VLP is highly similar to natural HPV in terms of structure, retains most of the neutralizing epitopes of natural virus, and can induce the generation of high-titer neutralizing antibodies (Kirnbauer, R., F. Booy, et al. 1992 Proc Natl Acad Sci USA 89(24): 12180-4).

However, the existing studies show that HPV VLPs mainly induce the generation of neutralizing antibodies against the same HPV type, produce the protective immunity against the same HPV type, and only have low cross-protective effect among a few highly homologous HPV types (Sara L. Bissett, Giada Mattiuzzo, et al. 2014 Vaccine. 32:6548-6555). Therefore, the existing HPV vaccines have a very limited protection range. In general, VLP of one HPV type can only be used to prevent infection by the same HPV type. In this case, if it needs to broaden the protection range of HPV vaccines, the only way is to add VLPs of more HPV types in vaccines. Currently, the commercially available HPV vaccines, including Gardasil® from Merck (which is a quadrivalent vaccine against HPV16, 18, 6 and 11), Cervarix® from GSK (which is a bivalent vaccine against HPV16 and 18), and Gardasil®9 from Merck (which is a 9-valent vaccine), are prepared by combining VLPs of multiple HPV types. However, such a solution would greatly increase the production cost of HPV vaccines, and might cause safety problem due to an increase in immunizing dose.

Therefore, it is urgent in the art to develop HPV virus-like particles capable of inducing the generation of protective neutralizing antibodies against multiple HPV types, so as to prevent infection by multiple HPV types, and a disease caused by the infection, such as cervical cancer and condyloma acuminatum, more economically and effectively.

Contents of Invention

The invention is at least partially based on the inventors' surprising discovery: after substitution of a specific segment of L1 protein of Human Papillomavirus (HPV) Type 11 with the corresponding segment of L1 protein of a second HPV type (such as HPV6), the mutated HPV11 L1 protein thus obtained can induce the generation of high-titer neutralizing antibodies against HPV11 and the second HPV type (such as HPV6) in organisms, and its protection effect is comparable to that of a mixture of HPV11 VLP and VLP of the second HPV type, its protection effect against HPV11 is comparable to that of HPV11 VLP alone, and its protection effect against the second HPV type (such as HPV6) is comparable to that of the VLP of the second HPV type alone.

Therefore, in one aspect, the invention provides a mutated HPV11 L1 protein or a variant thereof, wherein as compared with wild type HPV11 L1 protein, the mutated HPV11 L1 protein has the following mutations:

(1) N-terminal truncation of 3-6 amino acids, for example, 3, 4, 5 or 6 amino acids; and (2) (a) substitution of amino acid residues at positions 170-179 of the wild type HPV11 L1 protein with amino acid residues at the corresponding positions of a L1 protein of a second type of wild-type HPV; or (b) substitution of amino acid residues at positions 346-351 of the wild type HPV11 L1 protein with amino acid residues at the corresponding positions of a L1 protein of a second type of wild-type HPV; or (c) substitution of amino acid residues at positions 119-140 of the wild type HPV11 L1 protein with amino acid residues at the corresponding positions of a L1 protein of a second type of wild-type HPV;

and, the variant differs from the mutated HPV11 L1 protein only by substitution (preferably conservative substitution), addition or deletion of one or several (e.g. 1, 2, 3, 4, 5, 6, 7, 8 or 9) amino acids, and retains the function of the mutated HPV11 L1 protein, i.e. capability of inducing generation of neutralizing antibodies against at least two HPV types (e.g. HPV11 and HPV6).

In some preferred embodiments, the mutated HPV11 L1 protein has 3, 4, 5 or 6 amino acids truncated at N-terminal, as compared with the wild type HPV11 L1 protein.

In some preferred embodiments, the mutated HPV11 L1 protein has 4 amino acids truncated at N-terminal, as compared with the wild type HPV11 L1 protein.

In some preferred embodiments, the second type of wild-type HPV is HPV6. In some preferred embodiments, the amino acid residues at the corresponding positions as described in (2) (a) are amino acid residues at positions 169-178 of a wild type HPV6 L1 protein.

In some preferred embodiments, the second type of wild-type HPV is HPV6. In some preferred embodiments, the amino acid residues at the corresponding positions as described in (2) (b) are amino acid residues at positions 345-350 of a wild type HPV6 L1 protein.

In some preferred embodiments, the second type of wild-type HPV is HPV6. In some preferred embodiments, the amino acid residues at the corresponding positions as described in (2) (c) are amino acid residues at positions 119-139 of a wild type HPV6 L1 protein.

In some preferred embodiments, the wild type HPV11 L1 protein has an amino acid sequence as set forth in SEQ ID NO: 1.

In some preferred embodiments, the wild type HPV6 L1 protein has an amino acid sequence as set forth in SEQ ID NO: 2.

In some preferred embodiments, the amino acid residues at positions 169 to 178 of the wild type HPV6 L1 protein have a sequence as set forth in SEQ ID NO: 35.

In some preferred embodiments, the amino acid residues at positions 345 to 350 of the wild type HPV6 L1 protein have a sequence as set forth in SEQ ID NO: 36.

In some preferred embodiments, the amino acid residues at positions 119 to 139 of the wild type HPV6 L1 protein have a sequence as set forth in SEQ ID NO: 37.

In some preferred embodiments, the mutated HPV11 L1 protein has an amino acid sequence selected from the group consisting of: SEQ ID NOs: 6, 7 and 9.

In another aspect, the invention provides an isolated nucleic acid encoding the mutated HPV11 L1 protein or a variant thereof as described above. In another aspect, the invention provides a vector comprising the isolated nucleic acid. In some preferred embodiments, the isolated nucleic acid according to the invention has a nucleotide sequence selected from the group consisting of: SEQ ID NOs: 13, 14 and 16.

Vectors useful for insertion of a polynucleotide of interest are well known in the art, including, but not limited to cloning vectors and expression vectors. In one embodiment, the vectors are, for example, plasmids, cosmids, phages, etc.

In another aspect, the invention further relates to a host cell comprising the isolated nucleic acid or the vector. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV virus-like particle comprising or consisting of the mutated HPV11 L1 protein or a variant thereof according to the invention.

In some preferred embodiments, the HPV virus-like particle according to the invention comprises the mutated HPV11 L1 protein, which has N-terminal truncation of 3-6 amino acids, for example, 3, 4, 5 or 6 amino acids, as compared to a wild type HPV11 L1 protein, and substitution of the amino acid residues at positions 170-179 of the wild type HPV11 L1 protein with the amino acid residues at positions 169-178 of a wild type HPV6 L1 protein.

In some preferred embodiments, the HPV virus-like particle according to the invention comprises the mutated HPV11 L1 protein, which has N-terminal truncation of 3-6 amino acids, for example, 3, 4, 5 or 6 amino acids, as compared to a wild type HPV11 L1 protein, and substitution of the amino acid residues at positions 346-351 of the wild type HPV11 L1 protein with the amino acid residues at positions 345-350 of a wild type HPV6 L1 protein.

In some preferred embodiments, the HPV virus-like particle according to the invention comprises the mutated HPV11 L1 protein, which has N-terminal truncation of 3-6 amino acids, for example, 3, 4, 5 or 6 amino acids, as compared to a wild type HPV11 L1 protein, and substitution of amino acid residues at positions 119-140 of the wild type HPV11 L1 protein with the amino acid residues at positions 119-139 of a wild type HPV6 L1 protein.

In a particularly preferred embodiment, the HPV virus-like particle according to the invention comprises the mutated HPV11 L1 protein, which has a sequence as set forth in SEQ ID NO: 6, 7 or 9.

In another aspect, the invention further relates to a composition comprising the mutated HPV11 L1 protein or a variant thereof, the isolated nucleic acid, the vector, the host cell, or the HPV virus-like particle. In some preferred embodiments, the composition comprises the mutated HPV11 L1 protein or a variant thereof according to the invention. In some preferred embodiments, the composition comprises the HPV virus-like particle according to the invention.

In another aspect, the invention further relates to a pharmaceutical composition or vaccine, comprising the HPV virus-like particle according to the invention, and optionally a pharmaceutically acceptable carrier and/or excipient. The pharmaceutical composition or vaccine according to the invention can be used for preventing HPV infection, or a disease caused by HPV infection, such as cervical cancer and condyloma acuminatum.

In some preferred embodiments, the HPV virus-like particle is present in an amount effective for preventing HPV infection or a disease caused by HPV infection. In some preferred embodiments, the HPV infection is infection by one or more HPV types (e.g. HPV11 infection and/or HPV6 infection). In some preferred embodiments, the disease caused by HPV infection is selected from the group consisting of cervical cancer and condyloma acuminatum.

The pharmaceutical composition or vaccine according to the invention may be administrated by methods well known in the art, for example, but not limited to, orally or by injection. In the invention, a particularly preferred administration route is injection.

In some preferred embodiments, the pharmaceutical composition or vaccine according to the invention is administrated in a form of a unit dosage. For example, but not for limiting the invention, each unit dosage contains 5 μg-80 μg, preferably 20 μg-40 μg of HPV virus-like particle.

In another aspect, the invention relates to a method for preparing the mutated HPV11 L1 protein or a variant thereof as described above, comprising expressing the mutated HPV11 L1 protein or a variant thereof in a host cell, and then recovering the mutated HPV11 L1 protein or a variant thereof from a culture of the host cell.

In some preferred embodiments, the host cell is *E. coli*.

In some preferred embodiments, the method comprises the steps of: expressing the mutated HPV11 L1 protein or a variant thereof in *E. coli*, and then obtaining the mutated HPV11 L1 protein or a variant thereof by purifying a lysate supernatant of the *E. coli*. In some preferred embodiments, the mutated HPV11 L1 protein or a variant thereof is recovered from the lysate supernatant of the *E. coli* by chromatography (e.g. cation-exchange chromatography, hydroxyapatite chromatography and/or hydrophobic interaction chromatography).

In another aspect, the invention relates to a method for preparing a vaccine, comprising combining the HPV virus-like particle according to the invention with a pharmaceutically acceptable carrier and/or excipient.

In another aspect, the invention relates to a method for preventing HPV infection or a disease caused by HPV infection, comprising administering to a subject a prophylactically effective amount of the HPV virus-like particle or the pharmaceutical composition or vaccine according to the invention. In a preferred embodiment, the HPV infection is infection by one or more HPV types (e.g. HPV11 infection and/or HPV6 infection). In another preferred embodiment, the disease caused by HPV infection includes, but is not limited to cervical cancer and condyloma acuminatum. In another preferred embodiment, the subject is mammal, such as human.

In another aspect, the invention further relates to use of the mutated HPV11 L1 protein or a variant thereof or the HPV virus-like particle according to the invention in the manufacture of a pharmaceutical composition or vaccine for preventing HPV infection or a disease caused by HPV infection. In a preferred embodiment, the HPV infection is infection by one or more HPV types (e.g. HPV11 infection and/or HPV6 infection). In another preferred embodiment, the disease caused by HPV infection includes, but is not limited to, cervical cancer and condyloma acuminatum.

Definitions of Terms in the Invention

In the invention, unless otherwise specified, the scientific and technical terms used herein have the meanings generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a second type of wild-type HPV" refers to a wild-type HPV type other than HPV11. In the invention, a second type of wild-type HPV is preferably wild-type HPV6.

According to the invention, the expression "corresponding positions" refers to the equivalent positions of the sequences being compared when the sequences are optimally aligned, i.e. the sequences are aligned to obtain a highest percentage of identity.

According to the invention, the term "wild type HPV11 L1 protein" refers to the naturally-occurring major capsid protein L1 in Human Papillomavirus Type 11 (HPV11). The sequence of wild type HPV11 L1 protein is well known in the art, and can be found in public database (such as HPV11 L1 protein encoded by Accession No. M14119.1, AF335603.1, AF335602.1, etc. in NCBI database).

In the invention, when an amino acid sequence of wild type HPV11 L1 protein is mentioned, it is described by reference to the sequence as set forth in SEQ ID NO: 1. For example, the expression "amino acid residues at positions 170-179 of a wild type HPV11 L1 protein" refers to the amino acid residues at positions 170-179 of the polypeptide as set forth in SEQ ID NO: 1. However, a person skilled in the art understands that wild type HPV11 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV11 isolates, and have substantively the same biological function. Therefore, in the invention, the term "wild type HPV11 L1 protein" includes not only the protein as set forth in SEQ ID NO: 1, but also L1 protein of various HPV11 isolates (such as HPV11 L1 protein encoded by Accession No. M14119.1, AF335603.1, AF335602.1, etc. in NCBI database). Moreover, when a sequence fragment of a wild type HPV11 L1 protein is described, it includes not only the sequence fragment of SEQ ID NO: 1, but also the corresponding sequence fragment of a L1 protein of various HPV11 isolates. For example, the expression "amino acid residues at positions 170-179 of a wild type HPV11 L1 protein" includes the amino acid residues at positions 170-179 of SEQ ID NO: 1, and the corresponding fragment of a L1 protein of various HPV11 isolates.

According to the invention, the term "wild type HPV6 L1 protein" refers to the naturally-occurring major capsid protein L1 in Human Papillomavirus Type 6 (HPV6). The sequence of wild type HPV6 L1 protein is well known in the art, and can be found in public database (such as HPV6 L1 protein encoded by Accession No. AF067042.1, AF092932.1, L41216.1, XOO203.1, etc. in NCBI database).

In the invention, when an amino acid sequence of wild type HPV6 L1 protein is mentioned, it is described by reference to the sequence as set forth in SEQ ID NO: 2. For example, the expression "amino acid residues at positions 169-178 of a wild type HPV6 L1 protein" refers to the amino acid residues at positions 169-178 of the polypeptide as set forth in SEQ ID NO: 2. However, a person skilled in the art understands that wild type HPV6 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV6 isolates, and have substantively the same biological function. Therefore, in the invention, the term "wild type HPV6 L1 protein" includes not only the protein as set forth in SEQ ID NO: 2, but also L1 protein of various HPV6 isolates (such as HPV6 L1 protein encoded by Accession No. AF067042.1, AF092932.1, L41216.1, XOO203.1, etc. in NCBI database). Moreover, when a sequence fragment of a wild type HPV6 L1 protein is described, it includes not only the sequence fragment of SEQ ID NO: 2, but also the corresponding sequence fragment of a L1 protein of various HPV6 isolates. For example, the expression "amino acid residues at positions 169-178 of a wild type HPV6 L1 protein" includes the amino acid residues at positions 169-178 of SEQ ID NO: 2, and the corresponding fragment of a L1 protein of various HPV6 isolates.

According to the invention, the expression "corresponding sequence fragments" or "corresponding fragments" refers to the fragments that are located in equivalent positions of the sequences being compared when the sequences are optimally aligned, i.e. the sequences are aligned to obtain a highest percentage of identity.

According to the invention, the expression "N-terminal truncation of X amino acids" or "having X amino acids truncated at N-terminal" refers to substitution of the amino acid residues from positions 1 to X at the N-terminal of a protein with methionine residue encoded by an initiator codon (for initiating protein translation). For example, a HPV11 L1 protein having 4 amino acids truncated at N-terminal refers to a protein resulted from substituting the amino acid residues from positions 1 to 4 at the N-terminal of wild type HPV11 L1 protein with methionine residue encoded by an initiator codon.

According to the invention, the term "variant" refers to a protein, whose amino acid sequence has substitution (preferably conservative substitution), addition or deletion of one or several (e.g. 1, 2, 3, 4, 5, 6, 7, 8 or 9) amino acids, or has an identity of at least 90%, 95%, 96%, 97%, 98%, or 99%, as compared with the mutated HPV11 L1 protein according to the invention (for example, the protein as set forth in SEQ ID NO: 6, 7 or 9), and which retains a function of the mutated HPV11 L1 protein. In the invention, the term "function of the mutated HPV11 L1 protein" refers to the capability of inducing the generation of neutralizing antibodies against at least two HPV types (e.g. HPV11 and HPV6). The term "identity" refers to a measure of similarity between nucleotide sequences or amino acid sequences. Generally, sequences were aligned to obtain a maximum matching. "Identity" has well-known meanings in the art and can be calculated by published algorithm (such as BLAST).

According to the invention, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the invention, the term "E. coli expression system" refers to an expression system consisting of E. coli (strain) and a vector, wherein the E. coli (strain) is derived from the commercially available strains, including, but not limited to: ER2566, BL21 (DE3), B834 (DE3), and BLR (DE3).

According to the invention, the term "vector" refers to a nucleic acid carrier tool which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, etc.

According to the invention, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants, e.g., Tween-80; adjuvants include, but are not limited to, aluminium adjuvant (e.g., aluminium hydroxide), and Freund's adjuvant (e.g., Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (such as cation-exchange chromatography), hydrophobic interaction chromatography, absorbent chromatography (such as hydroxyapatite chromatography), gel filtration chromatography (gel exclusion chromatography), and affinity chromatography.

According to the invention, the term "lysate supernatant" refers to a solution produced by the following steps: host cells (such as E. coli) are disrupted in a lysis buffer, and the insoluble substances are then removed from the lysed solution containing the disrupted host cells. Various lysis buffers are well known in the art, including, but not limited to Tris buffers, phosphate buffers, HEPES buffers, MOPS buffers, etc. In addition, the disrupting of a host cell can be accomplished by methods well known by a person skilled in the art, including, but not limited to homogenizer disrupting, ultrasonic treatment, grinding, high pressure extrusion, lysozyme treatment, etc. Methods for removing insoluble substances are also well known by a person skilled in the art, including, but not limited to filtration and centrifugation.

Beneficial Effects of Invention

Studies show that although there is certain cross-protection between HPV11 and other HPV type(s) (such as HPV6), such cross-protection is very low, generally lower than one percent, even one thousandth of the protection level of VLP of the same HPV type. Therefore, a subject vaccinated with HPV11 vaccine, still has a high risk of being infected by other HPV type(s) (such as HPV6).

The invention provides a mutated HPV11 L1 protein and a HPV virus-like particle formed by the same. The HPV virus-like particle according to the invention can provide significant cross-protection against HPV11 and other HPV type(s) (such as HPV6). Especially, at the same immunizing dose, the HPV virus-like particle according to the invention can induce the generation of high-titer neutralizing antibodies against at least two HPV types (e.g. HPV11 and HPV6) in organisms, and its effect is comparable to that of a mixture of VLPs of multiple HPV types (e.g. a mixture of HPV11 VLP and HPV6 VLP). Therefore, the HPV virus-like particle according to the invention can be used to prevent infection by at least two HPV types (e.g. HPV11 and HPV6) at the same time as well as diseases associated with the infection, and has significantly beneficial technical effects. This has particularly significant advantages in terms of extending the protection range of HPV vaccines and reducing the production cost of HPV vaccines.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF DRAWINGS

FIG. 2A: HPV11N4; FIG. 2B: H11N4-6T1; FIG. 2C: H11N4-6T2; FIG. 2D: H11N4-6T3; FIG. 2E: H11N4-6T4; FIG. 2F: H11N4-6T5. The results showed that the first protein peak of the samples comprising H11N4-6T1, H11N4-6T2, H11N4-6T3, H11N4-6T4 and H11N4-6T5 respectively appeared at about 12 min, which was comparable to that of HPV11N4 VLP. This showed that all these mutated proteins were able to assemble into VLPs.

FIG. 3A, HPV11N4 VLP; FIG. 3B, H11N4-6T1 VLP; FIG. 3C, H11N4-6T2 VLP; FIG. 3D, H11N4-6T3 VLP; FIG. 3E, H11N4-6T4 VLP; FIG. 3F, H11N4-6T5 VLP. The results showed that the sedimentation coefficient of H11N4-6T1 VLP, H11N4-6T2 VLP, H11N4-6T3 VLP, H11N4-6T4 VLP and H11N4-6T5 VLP was 140S, 138S, 111S, 139S and 139S, respectively. This indicated that the 5 mutated HPV11 L1 proteins as prepared above were able to assemble into virus-like particles that were similar to wild type VLP (HPV11N4 VLP, 136.3S) in terms of size and morphology.

FIG. 4A, HPV11N4 VLP; FIG. 4B, H11N4-6T1 VLP; FIG. 4C, H11N4-6T2 VLP; FIG. 4D, H11N4-6T3 VLP; FIG. 4E, H11N4-6T4 VLP; FIG. 4F, H11N4-6T5 VLP. The results showed that H11N4-6T1, H11N4-6T2, H11N4-6T3, H11N4-6T4 and H11N4-6T5 were similar to HPV11N4, and were able to assemble into VLPs with a radius of about 25 nm.

FIG. 5A, HPV11N4 VLP; FIG. 5B, H11N4-6T1 VLP; FIG. 5C, H11N4-6T2 VLP; FIG. 5D, H11N4-6T3 VLP; FIG. 5E, H11N4-6T4 VLP; FIG. 5F, H11N4-6T5 VLP. The results showed that all the VLPs formed by these proteins had very high thermostability.

FIGS. 6A-6D show the cryo-electron microscopy (cryoEM) photographs and the analyzed structures of H11N4-6T3 VLP and H11N4-6T5 VLP; wherein, FIG. 6A and FIG. 6C show the cryo-electron microscopy (cryoEM) photographs of H11N4-6T3 VLP and H11N4-6T5 VLP, respectively; FIG. 6B and FIG. 6D show the three-dimensional structures of H11N4-6T3 VLP and H11N4-6T5 VLP as analyzed by using cryo-electron microscopy (cryoEM), at a resolution of 17.38 Å and 20.48 Å, respectively.

FIG. 8A: Aluminum adjuvant group 1 (at an immunizing dose of 10 μg, using aluminum adjuvant); FIG. 8B: Aluminum adjuvant group 2 (at an immunizing dose of 1 μg, using aluminum adjuvant); FIG. 8C: Aluminum adjuvant group 3 (at an immunizing dose of 0.1 μg, using aluminum adjuvant). The results showed that either of H11N4-6T3 VLP and H11N4-6T5 VLP could induce the generation of high-titer neutralizing antibodies against HPV11 in mice, and their protective effects were comparable to that of HPV11N4 VLP alone or the mixed HPV11/HPV6 VLP at the same dose, and were significantly superior to that of HPV6N5 VLP alone at the same dose; and they could induce the generation of high-titer neutralizing antibodies against HPV6 in mice, and their protective effects were comparable to that of HPV6N5 VLP alone or the mixed HPV11/HPV6 VLP at the same dose, and were significantly superior to that of HPV11N4 VLP alone at the same dose. This showed that H11N4-6T3 VLP and H11N4-6T5 VLP had good cross-immunogenicity and cross-protection against HPV11 and HPV6.

SEQUENCE INFORMATION

Figure 1:
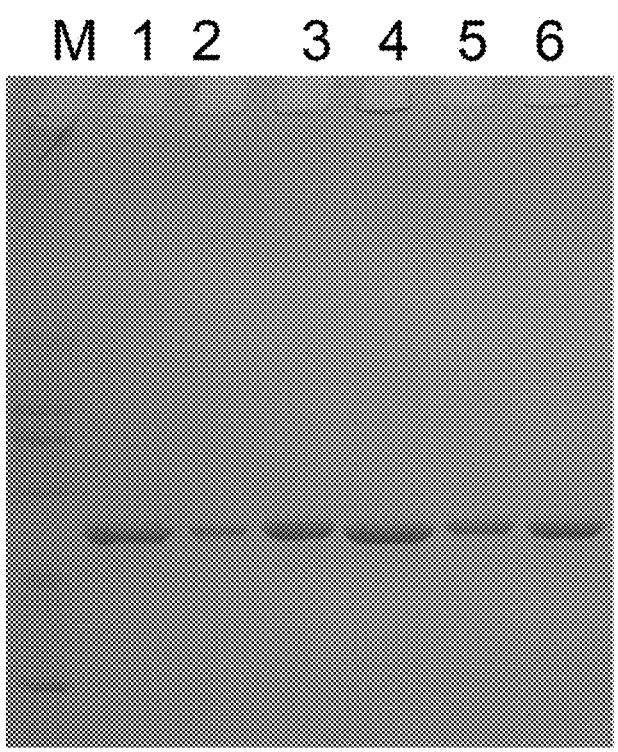
FIG. 1 shows the SDS-PAGE result of the purified mutated proteins in Example 1. Lane M: protein molecular weight marker; Lane 1: HPV11N4 (HPV11 L1 protein having 4 amino acids truncated at N-terminal); Lane 2: H11N4-6T1; Lane 3: H11N4-6T2; Lane 4: H11N4-6T3; Lane 5: H11N4-6T4; Lane 6: H11N4-6T5. The result showed that after chromatographic purification, the proteins H11N4-6T1, H11N4-6T2, H11N4-6T3, H11N4-6T4 and H11N4-6T5 reached a purity of above 95%.
Figure 2:
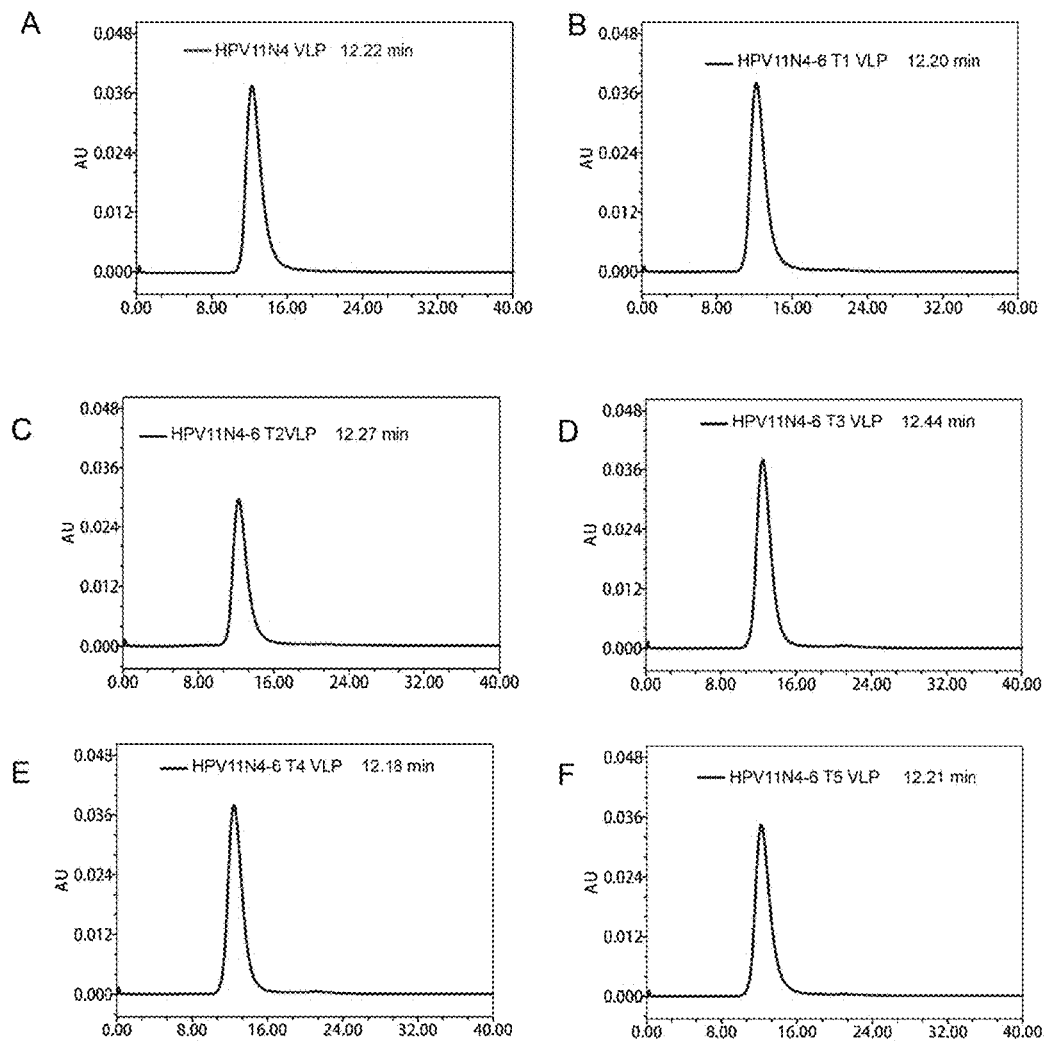
FIGS. 2A-2F show the results of molecular sieve chromatographic analysis of the samples comprising the protein HPV11N4, H11N4-6T1, H11N4-6T2, H11N4-6T3, H11N4-6T4 and H11N4-6T5, respectively.
Figure 3:
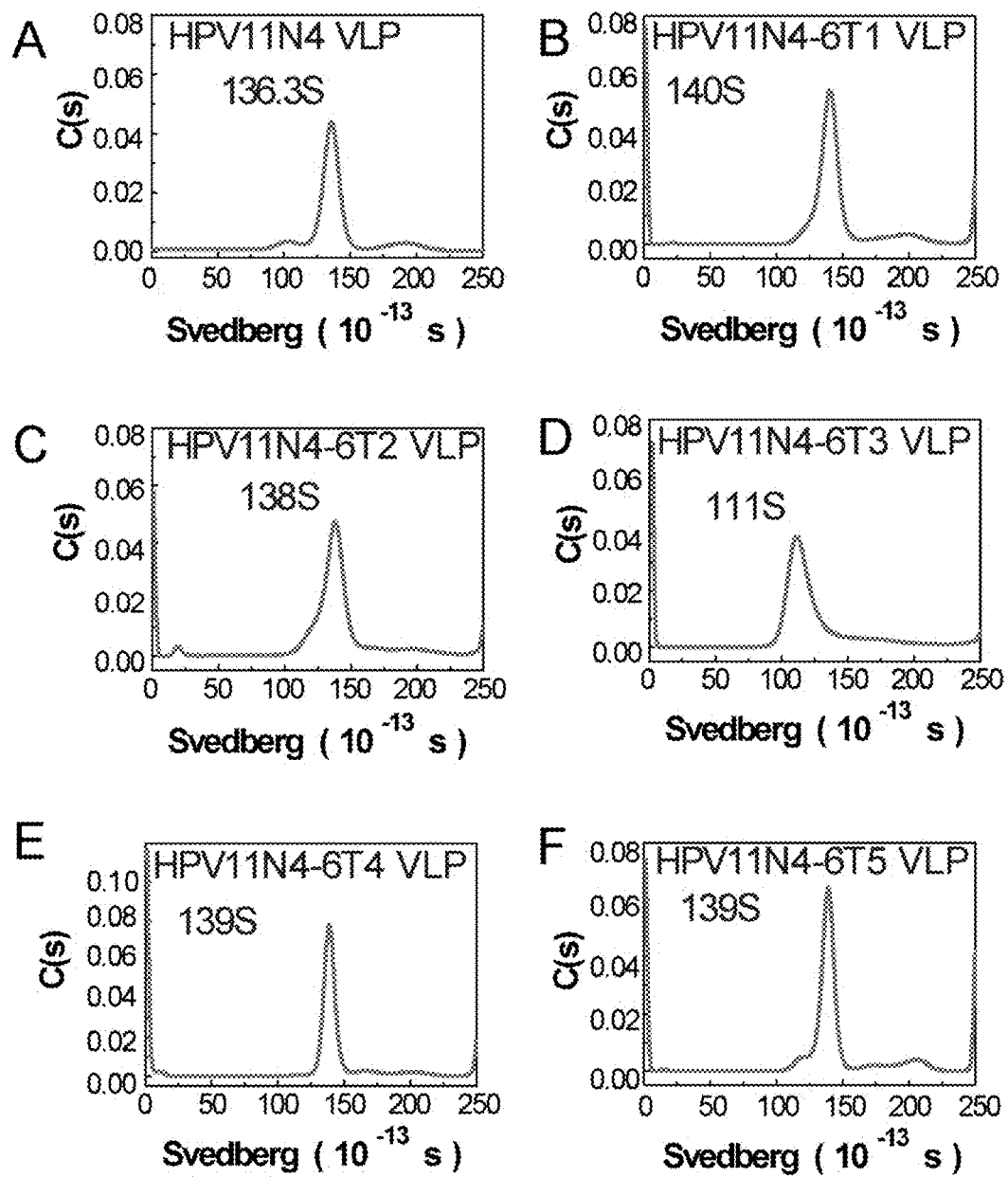
FIGS. 3A-3F show the results of sedimentation velocity analysis of HPV11N4 VLP, H11N4-6T1 VLP, H11N4-6T2 VLP, H11N4-6T3 VLP, H11N4-6T4 VLP and H11N4-6T5 VLP.
Figure 4:
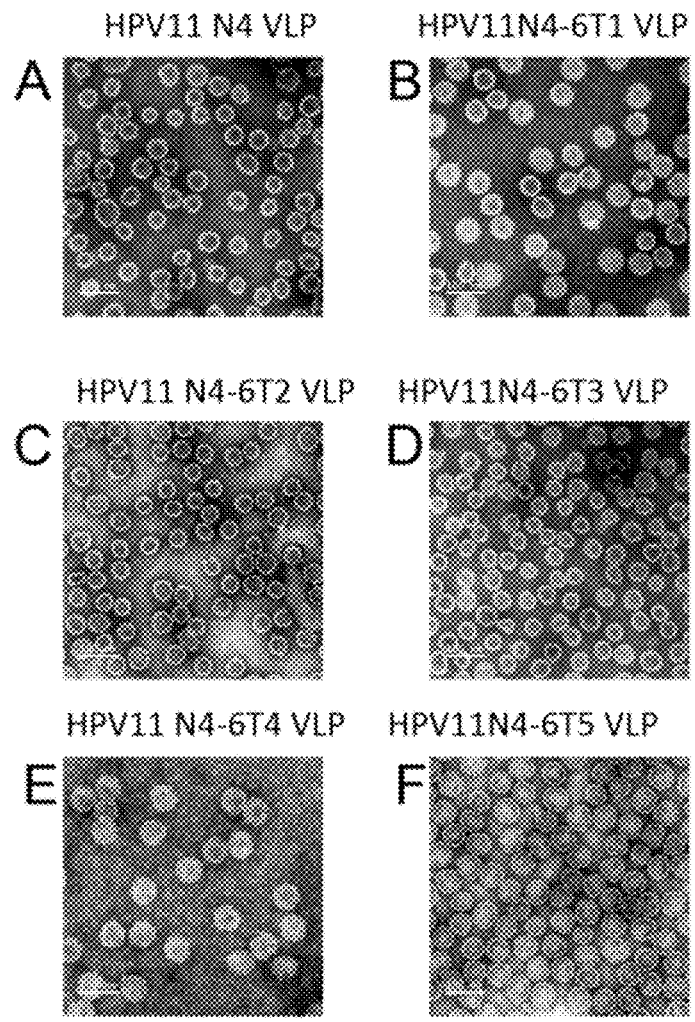
FIGS. 4A-4F show the transmission electron microscopy (TEM) photographs (taken at 100,000× magnification, Bar=0.1 μm) of various VLP samples.
Figure 5:
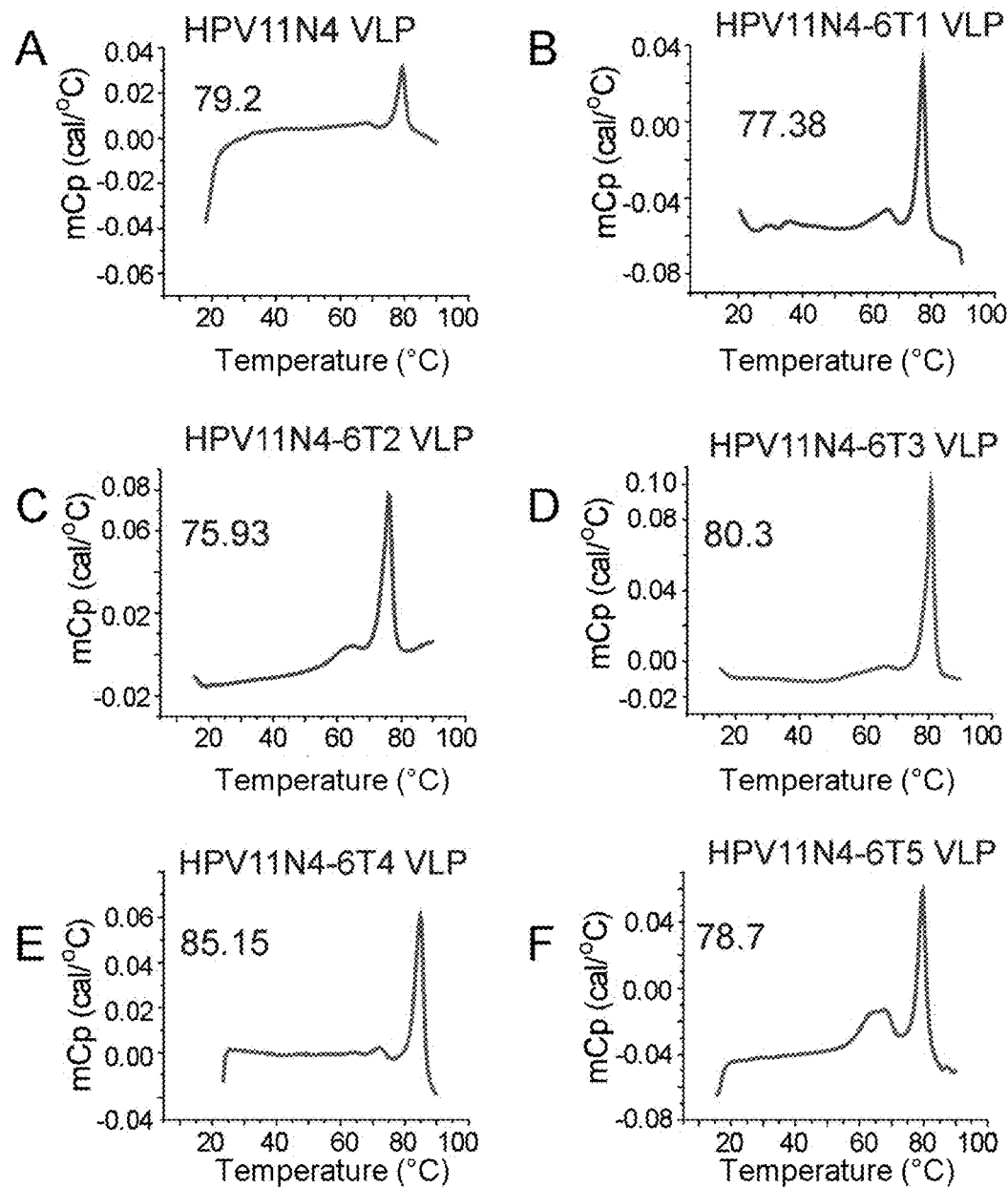
FIGS. 5A-5F show the results of thermostability evaluation of VLPs formed by HPV11N4, H11N4-6T1, H11N4-6T2, H11N4-6T3, H11N4-6T4 and H11N4-6T5 respectively.

Some of the sequences involved in the invention are provided in the following Table 1.

TABLE 1

| SEQ ID NO: | Description |
|---|---|
| 1 | wild type HPV11 L1 protein |
| 2 | wild type HPV6 L1 protein |
| 3 | the HPV11 L1 protein having 4 amino acids truncated at N-terminal, HPV11N4 |
| 4 | the HPV6 L1 protein having 5 amino acids truncated at N-terminal, HPV6N5 |
| 5 | the mutated HPV11 L1 protein comprising Segment 1 of HPV6 L1 protein, H11N4-6T1 |
| 6 | the mutated HPV11 L1 protein comprising Segment 2 of HPV6 L1 protein, H11N4-6T2 |
| 7 | the mutated HPV11 L1 protein comprising Segment 3 of HPV6 L1 protein, H11N4-6T3 |
| 8 | the mutated HPV11 L1 protein comprising Segment 4 of HPV6 L1 protein, H11N4-6T4 |
| 9 | the mutated HPV11 L1 protein comprising Segment 5 of HPV6 L1 protein, H11N4-6T5 |
| 10 | the DNA sequence encoding SEQ ID NO: 3 |
| 11 | the DNA sequence encoding SEQ ID NO: 4 |
| 12 | the DNA sequence encoding SEQ ID NO: 5 |
| 13 | the DNA sequence encoding SEQ ID NO: 6 |
| 14 | the DNA sequence encoding SEQ ID NO: 7 |
| 15 | the DNA sequence encoding SEQ ID NO: 8 |
| 16 | the DNA sequence encoding SEQ ID NO: 9 |
| 35 | the sequence of amino acid residues at positions 169 to 178 of wild type HPV6 L1 protein |
| 36 | the sequence of amino acid residues at positions 345 to 350 of wild type HPV6 L1 protein |
| 37 | the sequence of amino acid residues at positions 119 to 139 of wild type HPV6 L1 protein |

```
Sequence 1 (SEQ ID NO: 1):
MWRPSDSTVYVPPPNPVSKVVATDAYVKRTNIFYHASSSRLLAVGHPYYSIKKVNKTVVPKVSGYQY

RVFKVVLPDPNKFALPDSSLFDPTTQRLVWACTGLEVGRGQPLGVGVSGHPLLNKYDDVENSGGYG

GNPGQDNRVNVGMDYKQTQLCMVGCAPPLGEHWGKGTQCSNTSVQNGDCPPLELITSVIQDGDMV

DTGFGAMNFADLQTNKSDVPLDICGTVCKYPDYLQMAADPYGDRLFFYLRKEQMFARHFFNRAGTV

GEPVPDDLLVKGGNNRSSVASSIYVHTPSGSLVSSEAQLFNKPYWLQKAQGHNNGICWGNHLFVTVV

DTTRSTNMTLCASVSKSATYTNSDYKEYMRHVEEFDLQFIFQLCSITLSAEVMAYIHTMNPSVLEDW

NFGLSPPPNGTLEDTYRYVQSQAITCQKPTPEKEKQDPYKDMSFWEVNLKEKFSSELDQFPLGRKFLL

QSGYRGRTSARTGIKRPAVSKPSTAPKRKRTKTKK

Sequence 2 (SEQ ID NO: 2):
MWRPSDSTVYVPPPNPVSKVVATDAYVTRTNIFYHASSSRLLAVGHPYFSIKRANKTVVPKVSGYQY

RVFKVVLPDPNKFALPDSSLFDPTTQRLVWACTGLEVGRGQPLGVGVSGHPFLNKYDDVENSGSGGN

PGQDNRVNVGMDYKQTQLCMVGCAPPLGEHWGKGKQCTNTPVQAGDCPPLELITSVIQDGDMVDT

GFGAMNFADLQTNKSDVPIDICGTTCKYPDYLQMAADPYGDRLFFFLRKEQMFARHFFNRAGEVGEP

VPDTLIIKGSGNRTSVGSSIYVNTPSGSLVSSEAQLFNKPYWLQKAQGHNNGICWGNQLFVTVVDTTR
```

-continued

STNMTLCASVTTSSTYTNSDYKEYMRHVEEYDLQFIFQLCSITLSAEVMAYIHTMNPSVLEDWNFGLS

PPPNGTLEDTYRYVQSQAITCQKPTPEKEKPDPYKNLSFWEVNLKEKFSSELDQYPLGRKFLLQSGYR

GRSSIRTGVKRPAVSKASAAPKRKRAKTKR

Sequence 3 (SEQ ID NO: 3):
MSDSTVYVPPPNPVSKVVATDAYVKRTNIFYHASSRLLAVGHPYYSIKKVNKTVVPKVSGYQYRVF

KVVLPDPNKFALPDSSLFDPTTQRLVWACTGLEVGRGQPLGVGVSGHPLLNKYDDVENSGGYGGNP

GQDNRVNVGMDYKQTQLCMVGCAPPLGEHWGKGTQCSNTSVQNGDCPPLELITSVIQDGDMVDTG

FGAMNFADLQTNKSDVPLDICGTVCKYPDYLQMAADPYGDRLFFYLRKEQMFARHFFNRAGTVGEP

VPDDLLVKGGNNRSSVASSIYVHTPSGSLVSSEAQLFNKPYWLQKAQGHNNGICWGNHLFVTVVDTT

RSTNMTLCASVSKSATYTNSDYKEYMRHVEEFDLQFIFQLCSITLSAEVMAYIHTMNPSVLEDWNFGL

SPPPNGTLEDTYRYVQSQAITCQKPTPEKEKQDPYKDMSFWEVNLKEKFSSELDQFPLGRKFLLQSGY

RGRTSARTGIKRPAVSKPSTAPKRKRTKTKK

Sequence 4 (SEQ ID NO: 4):
MDSTVYVPPPNPVSKVVATDAYVTRTNIFYHASSRLLAVGHPYFSIKRANKTVVPKVSGYQYRVFK

VVLPDPNKFALPDSSLFDPTTQRLVWACTGLEVGRGQPLGVGVSGHPFLNKYDDVENSGSGGNPGQ

DNRVNVGMDYKQTQLCMVGCAPPLGEHWGKGKQCTNTPVQAGDCPPLELITSVIQDGDMVDTGFG

AMNFADLQTNKSDVPIDICGTTCKYPDYLQMAADPYGDRLFFFLRKEQMFARHFFNRAGEVGEPVPD

TLIIKGSGNRTSVGSSIYVNTPSGSLVSSEAQLFNKPYWLQKAQGHNNGICWGNQLFVTVVDTTRSTN

MTLCASVTTSSTYTNSDYKEYMRHVEEYDLQFIFQLCSITLSAEVVAYIHTMNPSVLEDWNFGLSPPP

NGTLEDTYRYVQSQAITCQKPTPEKQKPDPYKNLSFWEVNLKEKFSSELDQYPLGRKFLLQSGYRGRS

SIRTGVKRPAVSKASAAPKRKRAKTKR

Sequence 5 (SEQ ID NO: 5):
MSDSTVYVPPPNPVSKVVATDAYVKRTNIFYHASSRLLAVGHPYFSIKRANKTVVPKVSGYQYRVF

KVVLPDPNKFALPDSSLFDPTTQRLVWACTGLEVGRGQPLGVGVSGHPLLNKYDDVENSGGYGGNP

GQDNRVNVGMDYKQTQLCMVGCAPPLGEHWGKGTQCSNTSVQNGDCPPLELITSVIQDGDMVDTG

FGAMNFADLQTNKSDVPLDICGTVCKYPDYLQMAADPYGDRLFFYLRKEQMFARHFFNRAGTVGEP

VPDDLLVKGGNNRSSVASSIYVHTPSGSLVSSEAQLFNKPYWLQKAQGHNNGICWGNHLFVTVVDTT

RSTNMTLCASVSKSATYTNSDYKEYMRHVEEFDLQFIFQLCSITLSAEVMAYIHTMNPSVLEDWNFGL

SPPPNGTLEDTYRYVQSQATTCQKPTPEKEKQDPYKDMSFWEVNLKEKFSSELDQFPLGRKFLLQSGY

RGRTSARTGIKRPAVSKPSTAPKRKRTKTKK

Sequence 6 (SEQ ID NO: 6):
MSDSTVYVPPPNPVSKVVATDAYVKRTNIFYHASSRLLAVGHPYYSIKKVNKTVVPKVSGYQYRVF

KVVLPDPNKFALPDSSLFDPTTQRLVWACTGLEVGRGQPLGVGVSGHPFLNKYDDVENSGSGGNPG

QDNRVNVGMDYKQTQLCMVGCAPPLGEHWGKGTQCSNTSVQNGDCPPLELITSVIQDGDMVDTGF

GAMNFADLQTNKSDVPLDICGTVCKYPDYLQMAADPYGDRLFFYLRKEQMFARHFFNRAGTVGEPV

PDDLLVKGGNNRSSVASSIYVHTPSGSLVSSEAQLFNKPYWLQKAQGHNNGICWGNHLFVTVVDTTR

STNMTLCASVSKSATYTNSDYKEYMRHVEEFDLQFIFQLCSITLSAEVMAYIHTMNPSVLEDWNFGLS

PPPNGTLEDTYRYVQSQAITCQKPTPEKEKQDPYKDMSFWEVNLKEKFSSELDQFPLGRKFLLQSGYR

GRTSARTGIKRPAVSKPSTAPKRKRTKTKK

Sequence 7 (SEQ ID NO: 7):
MSDSTVYVPPPNPVSKVVATDAYVKRTNIFYHASSRLLAVGHPYYSIKKVNKTVVPKVSGYQYRVF

KVVLPDPNKFALPDSSLFDPTTQRLVWACTGLEVGRGQPLGVGVSGHPLLNKYDDVENSGGYGGNP

GQDNRVNVGMDYKQTQLCMVGCAPPLGEHWGKGKQCTNTPVQAGDCPPLELITSVIQDGDMVDTG

-continued

```
FGAMNFADLQTNKSDVPLDICGTVCKYPDYLQMAADPYGDRLFFYLRKEQMFARHFFNRAGTVGEP
VPDDLLVKGGNNRSSVASSIYVHTPSGSLVSSEAQLFNKPYWLQKAQGHNNGICWGNHLFVTVVDTT
RSTNMTLCASVSKSATYTNSDYKEYMRHVEEFDLQFIFQLCSITLSAEVMAYIHTMNPSVLEDWNFGL
SPPPNGTLEDTYRYVQSQAITCQKPTPEKEKQDPYKDMSFWEVNLKEKFSSELDQFPLGRKFLLQSGY
RGRTSARTGIKRPAVSKPSTAPKRKRTKTKK

Sequence 8 (SEQ ID NO: 8):
MSDSTVYVPPPNPVSKVVATDAYVKRTNIFYHASSSRLLAVGHPYYSIKKVNKTVVPKVSGYQYRVF
KVVLPDPNKFALPDSSLFDPTTQRLVWACTGLEVGRGQPLGVGVSGHPLLNKYDDVENSGGYGGNP
GQDNRVNVGMDYKQTQLCMVGCAPPLGEHWGKGTQCSNTSVQNGDCPPLELITSVIQDGDMVDTG
FGAMNFADLQTNKSDVPLDICGTVCKYPDYLQMAADPYGDRLFFYLRKEQMFARHFFNRAGEVGEP
VPDTLIIKGSGNRTSVGSSIYVHTPSGSLVSSEAQLFNKPYWLQKAQGHNNGICWGNHLFVTVVDTTR
STNMTLCASVSKSATYTNSDYKEYMRHVEEFDLQFIFQLCSITLSAEVMAYIHTMNPSVLEDWNFGLS
PPPNGTLEDTYRYVQSQAITCQKPTPEKEKQDPYKDMSFWEVNLKEKFSSELDQFPLGRKFLLQSGYR
GRTSARTGIKRPAVSKPSTAPKRKRTKTKK Sequence 9 (SEQ ID NO: 9):
MSDSTVYVPPPNPVSKVVATDAYVKRTNIFYHASSSRLLAVGHPYYSIKKVNKTVVPKVSGYQYRVF
KVVLPDPNKFALPDSSLFDPTTQRLVWACTGLEVGRGQPLGVGVSGHPLLNKYDDVENSGGYGGNP
GQDNRVNVGMDYKQTQLCMVGCAPPLGEHWGKGTQCSNTSVQNGDCPPLELITSVIQDGDMVDTG
FGAMNFADLQTNKSDVPLDICGTVCKYPDYLQMAADPYGDRLFFYLRKEQMFARHFFNRAGTVGEP
VPDDLLVKGGNNRSSVASSIYVHTPSGSLVSSEAQLFNKPYWLQKAQGHNNGICWGNHLFVTVVDTT
RSTNMTLCASVTTSSTYTNSDYKEYMRHVEEFDLQFIFQLCSITLSAEVMAYIHTMNPSVLEDWNFGL
S
PPPNGTLEDTYRYVQSQATTCQKPTPEKEKQDPYKDMSFWEVNLKEKFSSELDQFPLGRKFLLQSGYR
GRTSARTGIKRPAVSKPSTAPKRKRTKTKK Sequence 10 (SEQ ID NO: 10):
ATGAGCGACAGCACAGTATATGTGCCTCCTCCCAACCCTGTATCCAAGGTTGTTGCCACGGATGC
GTATGTTAAACGCACCAACATATTTTATCACGCCAGCAGTTCTAGACTCCTTGCTGTGGGACATCC
ATATTACTCTATCAAAAAAGTTAACAAAACAGTTGTACCAAAGGTGTCTGGATATCAATATAGAG
TGTTTAAGGTAGTGTTGCCAGATCCTAACAAGTTTGCATTACCTGATTCATCTCTGTTTGACCCCA
CTACACAGCGTTTAGTATGGGCGTGCACAGGGTTGGAGGTAGGCAGGGGTCAACCTTTAGGCGTT
GGTGTTAGTGGGCATCCATTGCTAAACAAATATGATGATGTAGAAAATAGTGGTGGGTATGGTGG
TAATCCTGGTCAGGATAATAGGGTTAATGTAGGTATGGATTATAAACAAACCCAGCTATGTATGG
TGGGCTGTGCTCCACCGTTAGGTGAACATTGGGGTAAGGGTACACAATGTTCAAATACCTCTGTA
CAAAATGGTGACTGCCCCCCGTTGGAACTTATTACCAGTGTTATACAGGATGGGACATGGTTGA
TACAGGCTTTGGTGCTATGAATTTTGCAGACTTACAAACCAATAAATCGGATGTTCCCCTTGATAT
TTGTGGAACTGTCTGCAAATATCCTGATTATTTGCAAATGGCAGCAGACCCTTATGGTGATAGGT
TGTTTTTTATTTGCGAAAGGAACAAATGTTTGCTAGACACTTTTTTAATAGGGCCGGTACTGTGG
GGGAACCTGTGCCTGATGACCTGTTGGTAAAAGGGGGTAATAATAGGTCATCTGTAGCTAGTAGT
ATTTATGTACATACACCTAGTGGATCCTTGGTGTCTTCAGAGGCTCAATTATTTAATAAACCATAT
TGGCTTCAAAAGGCTCAGGGACATAACAATGGTATTTGCTGGGGAAACCACTTGTTTGTTACTGT
GGTAGATACCACACGCAGTACAAATATGACACTATGTGCATCTGTGTCTAAATCTGCTACATACA
CTAATTCAGATTATAAGGAATATATGCGCCATGTGGAGGAGTTTGATTTACAGTTTATTTTTCAAT
```

-continued

TGTGTAGCATTACATTATCTGCAGAAGTCATGGCCTATATACACACAATGAATCCTTCTGTTTTGG
AGGACTGGAACTTTGGTTTATCGCCTCCACCAAATGGTACACTGGAGGATACTTATAGATATGTA
CAGTCACAGGCCATTACCTGTCAGAAACCCACACCCGAAAAAGAAAAACAGGACCCCTATAAGG
ATATGAGTTTTTGGGAGGTTAACTTAAAAGAAAAGTTTTCTTCTGAATTAGATCAGTTTCCCCTTG
GACGTAAGTTTTTATTGCAAAGTGGATATCGAGGACGGACGTCTGCTCGTACAGGTATAAAGCGC
CCAGCTGTGTCTAAGCCCTCTACAGCCCCCAAACGAAAACGTACCAAAACCAAAAAGTAA

Sequence 11 (SEQ ID NO: 11):
ATGGACAGCACAGTATATGTGCCTCCTCCTAACCCTGTATCCAAAGTTGTTGCCACGGATGCTTAT
GTTACTCGCACCAACATATTTTATCATGCCAGCAGTTCTAGACTTCTTGCAGTGGGTCATCCTTAT
TTTTCCATAAAACGGGCTAACAAAACTGTTGTGCCAAAGGTGTCAGGATATCAATACAGGGTATT
TAAGGTGGTGTTACCAGATCCTAACAAATTTGCATTGCCTGACTCGTCTCTTTTTGATCCCACAAC
ACAACGTTTGGTATGGGCATGCACAGGCCTAGAGGTGGGCAGGGACAGCCATTAGGTGTGGGT
GTAAGTGGACATCCTTTCCTAAATAAATATGATGATGTTGAAAATTCAGGGAGTGGTGGTAACCC
TGGACAGGATAACAGGGTTAATGTTGGTATGGATTATAAACAAACACAATTATGCATGGTTGGAT
GTGCCCCCCTTTGGGCGAGCATTGGGGTAAAGGTAAACAGTGTACTAATACACCTGTACAGGCT
GGTGACTGCCCGCCCTTAGAACTTATTACCAGTGTTATACAGGATGGCGATATGGTTGACACAGG
CTTTGGTGCTATGAATTTTGCTGATTTGCAGACCAATAAATCAGATGTTCCTATTGATATATGTGG
CACTACATGTAAATATCCAGATTATTTACAAATGGCTGCAGACCCTTATGGTGATAGATTATTTTT
TTTTCTACGGAAGGAACAAATGTTTGCCAGACATTTTTTTAACAGGGCTGGCGAGGTGGGGGAAC
CTGTGCCTGATACTCTTATAATTAAGGGTAGTGGAAATCGAACGTCTGTAGGGAGTAGTATATAT
GTTAACACCCCAAGCGGCTCTTTGGTGTCCTCTGAGGCACAATTGTTTAATAAGCCATATTGGCTA
CAAAAAGCCCAGGGACATAACAATGGTATTTGTTGGGGTAATCAACTGTTTGTTACTGTGGTAGA
TACCACACGCAGTACCAACATGACATTATGTGCATCCGTAACTACATCTTCCACATACACCAATT
CTGATTATAAAGAGTACATGCGTCATGTGGAAGAGTATGATTTACAATTTATTTTTCAATTATGTA
GCATTACATTGTCTGCTGAAGTAGTGGCCTATATTCACACAATGAATCCCTCTGTTTTGGAAGACT
GGAACTTTGGGTTATCGCCTCCCCCAAATGGTACATTAGAAGATACCTATAGGTATGTGCAGTCA
CAGGCCATTACCTGTCAAAAGCCCACTCCTGAAAAGCAAAGCCAGATCCCTATAAGAACCTTA
GTTTTTGGGAGGTTAATTTAAAAGAAAAGTTTTCTAGTGAATTGGATCAGTATCCTTTGGGACGC
AAGTTTTTGTTACAAAGTGGATATAGGGGACGGTCCTCTATTCGTACCGGTGTTAAGCGCCCTGC
TGTTTCCAAAGCCTCTGCTGCCCCTAAACGTAAGCGCGCCAAAACTAAAAGGTAA Sequence 12 (SEQ ID NO: 12):
ATGAGCGACAGCACAGTATATGTGCCTCCTCCCAACCCTGTATCCAAGGTTGTTGCCACGGATGC
GTATGTTAAACGCACCAACATATTTTATCACGCCAGCAGTTCTAGACTCCTTGCTGTGGGACATCC
ATATTTTTCCATAAAACGGGCTAACAAAACTGTTGTGCCAAAGGTGTCAGGATATCAATATAGAG
TGTTTAAGGTAGTGTTGCCAGATCCTAACAAGTTTGCATTACCTGATTCATCTCTGTTTGACCCCA
CTACACAGCGTTTAGTATGGGCGTGCACAGGGTTGGAGGTAGGCAGGGGTCAACCTTTAGGCGTT
GGTGTTAGTGGGCATCCATTGCTAAACAAATATGATGATGTAGAAAATAGTGGTGGGTATGGTGG
TAATCCTGGTCAGGATAATAGGGTTAATGTAGGTATGGATTATAAACAAACCCAGCTATGTATGG
TGGGCTGTGCTCCACCGTTAGGTGAACATTGGGGTAAGGGTACACAATGTTCAAATACCTCTGTA
CAAAATGGTGACTGCCCCCCGTTGGAACTTATTACCAGTGTTATACAGGATGGGGACATGGTTGA
TACAGGCTTTGGTGCTATGAATTTTGCAGACTTACAAACCAATAAATCGGATGTTCCCCTTGATAT
TTGTGGAACTGTCTGCAAATATCCTGATTATTTGCAAATGGCAGCAGACCCTTATGGTGATAGGT -continued

```
TGTTTTTTTATTTGCGAAAGGAACAAATGTTTGCTAGACACTTTTTTAATAGGGCCGGTACTGTGG

GGGAACCTGTGCCTGATGACCTGTTGGTAAAAGGGGGTAATAATAGGTCATCTGTAGCTAGTAGT

ATTTATGTACATACACCTAGTGGATCCTTGGTGTCTTCAGAGGCTCAATTATTTAATAAACCATAT

TGGCTTCAAAAGGCTCAGGGACATAACAATGGTATTTGCTGGGGAAACCACTTGTTTGTTACTGT

GGTAGATACCACACGCAGTACAAATATGACACTATGTGCATCTGTGTCTAAATCTGCTACATACA

CTAATTCAGATTATAAGGAATATATGCGCCATGTGGAGGAGTTTGATTTACAGTTTATTTTTCAAT

TGTGTAGCATTACATTATCTGCAGAAGTCATGGCCTATATACACACAATGAATCCTTCTGTTTTGG

AGGACTGGAACTTTGGTTTATCGCCTCCACCAAATGGTACACTGGAGGATACTTATAGATATGTA

CAGTCACAGGCCATTACCTGTCAGAAACCCACACCCGAAAAAGAAAAACAGGACCCCTATAAGG

ATATGAGTTTTTGGGAGGTTAACTTAAAAGAAAAGTTTTCTTCTGAATTAGATCAGTTTCCCCTTG

GACGTAAGTTTTTATTGCAAAGTGGATATCGAGGACGGACGTCTGCTCGTACAGGTATAAAGCGC

CCAGCTGTGTCTAAGCCCTCTACAGCCCCCAAACGAAAACGTACCAAAACCAAAAGTAA
```

Sequence 13 (SEQ ID NO: 13):
```
ATGAGCGACAGCACAGTATATGTGCCTCCTCCCAACCCTGTATCCAAGGTTGTTGCCACGGATGC

GTATGTTAAACGCACCAACATATTTTATCACGCCAGCAGTTCTAGACTCCTTGCTGTGGGACATCC

ATATTACTCTATCAAAAAGTTAACAAAACAGTTGTACCAAAGGTGTCTGGATATCAATATAGAG

TGTTTAAGGTAGTGTTGCCAGATCCTAACAAGTTTGCATTACCTGATTCATCTCTGTTTGACCCCA

CTACACAGCGTTTAGTATGGGCGTGCACAGGGTTGGAGGTAGGCAGGGGACAGCCATTAGGTGT

GGGTGTAAGTGGACATCCTTTCCTAAATAAATATGATGATGTTGAAAATTCAGGGAGTGGTGGTA

ACCCTGGACAGGATAACAGGGTTAATGTTGGTATGGATTATAAACAAACCCAGCTATGTATGGTG

GGCTGTGCTCCACCGTTAGGTGAACATTGGGGTAAGGGTACACAATGTTCAAATACCTCTGTACA

AAATGGTGACTGCCCCCCGTTGGAACTTATTACCAGTGTTATACAGGATGGGGACATGGTTGATA

CAGGCTTTGGTGCTATGAATTTTGCAGACTTACAAACCAATAAATCGGATGTTCCCCTTGATATTT

GTGGAACTGTCTGCAAATATCCTGATTATTTGCAAATGGCAGCAGACCCTTATGGTGATAGGTTG

TTTTTTTATTTGCGAAAGGAACAAATGTTTGCTAGACACTTTTTTAATAGGGCCGGTACTGTGGG

GAACCTGTGCCTGATGACCTGTTGGTAAAAGGGGGTAATAATAGGTCATCTGTAGCTAGTAGTAT

TTATGTACATACACCTAGTGGATCCTTGGTGTCTTCAGAGGCTCAATTATTTAATAAACCATATTG

GCTTCAAAAGGCTCAGGGACATAACAATGGTATTTGCTGGGGAAACCACTTGTTTGTTACTGTGG

TAGATACCACACGCAGTACAAATATGACACTATGTGCATCTGTGTCTAAATCTGCTACATACACT

AATTCAGATTATAAGGAATATATGCGCCATGTGGAGGAGTTTGATTTACAGTTTATTTTTCAATTG

TGTAGCATTACATTATCTGCAGAAGTCATGGCCTATATACACACAATGAATCCTTCTGTTTTGGAG

GACTGGAACTTTGGTTTATCGCCTCCACCAAATGGTACACTGGAGGATACTTATAGATATGTACA

GTCACAGGCCATTACCTGTCAGAAACCCACACCCGAAAAAGAAAAACAGGACCCCTATAAGGAT

ATGAGTTTTTGGGAGGTTAACTTAAAAGAAAAGTTTTCTTCTGAATTAGATCAGTTTCCCCTTGGA

CGTAAGTTTTTATTGCAAAGTGGATATCGAGGACGGACGTCTGCTCGTACAGGTATAAAGCGCCC

AGCTGTGTCTAAGCCCTCTACAGCCCCCAAACGAAAACGTACCAAAACCAAAAGTAA
```

Sequence 14 (SEQ ID NO: 14):
```
ATGAGCGACAGCACAGTATATGTGCCTCCTCCCAACCCTGTATCCAAGGTTGTTGCCACGGATGC

GTATGTTAAACGCACCAACATATTTTATCACGCCAGCAGTTCTAGACTCCTTGCTGTGGGACATCC

ATATTACTCTATCAAAAAGTTAACAAAACAGTTGTACCAAAGGTGTCTGGATATCAATATAGAG

TGTTTAAGGTAGTGTTGCCAGATCCTAACAAGTTTGCATTACCTGATTCATCTCTGTTTGACCCCA
```

-continued

CTACACAGCGTTTAGTATGGGCGTGCACAGGGTTGGAGGTAGGCAGGGGTCAACCTTTAGGCGTT

GGTGTTAGTGGGCATCCATTGCTAAACAAATATGATGATGTAGAAAATAGTGGTGGGTATGGTGG

TAATCCTGGTCAGGATAATAGGGTTAATGTAGGTATGGATTATAAACAAACCCAGCTATGTATGG

TGGGCTGTGCTCCACCGTTAGGTGAACATTGGGGTAAAGGTAAACAGTGTACTAATACACCTGTA

CAGGCTGGTGACTGCCCGCCCTTGGAACTTATTACCAGTGTTATACAGGATGGGGACATGGTTGA

TACAGGCTTTGGTGCTATGAATTTTGCAGACTTACAAACCAATAAATCGGATGTTCCCCTTGATAT

TTGTGGAACTGTCTGCAAATATCCTGATTATTTGCAAATGGCAGCAGACCCTTATGGTGATAGGT

TGTTTTTTATTTGCGAAAGGAACAAATGTTTGCTAGACACTTTTTTAATAGGGCCGGTACTGTGG

GGGAACCTGTGCCTGATGACCTGTTGGTAAAAGGGGGTAATAATAGGTCATCTGTAGCTAGTAGT

ATTTATGTACATACACCTAGTGGATCCTTGGTGTCTTCAGAGGCTCAATTATTTAATAAACCATAT

TGGCTTCAAAAGGCTCAGGGACATAACAATGGTATTTGCTGGGGAAACCACTTGTTTGTTACTGT

GGTAGATACCACACGCAGTACAAATATGACACTATGTGCATCTGTGTCTAAATCTGCTACATACA

CTAATTCAGATTATAAGGAATATATGCGCCATGTGGAGGAGTTTGATTTACAGTTTATTTTTCAAT

TGTGTAGCATTACATTATCTGCAGAAGTCATGGCCTATATACACACAATGAATCCTTCTGTTTTGG

AGGACTGGAACTTTGGTTTATCGCCTCCACCAAATGGTACACTGGAGGATACTTATAGATATGTA

CAGTCACAGGCCATTACCTGTCAGAAACCCACACCCGAAAAGAAAAACAGGACCCCTATAAGG

ATATGAGTTTTTGGGAGGTTAACTTAAAAGAAAAGTTTTCTTCTGAATTAGATCAGTTTCCCCTTG

GACGTAAGTTTTTATTGCAAAGTGGATATCGAGGACGGACGTCTGCTCGTACAGGTATAAAGCGC

CCAGCTGTGTCTAAGCCCTCTACAGCCCCCAAACGAAAACGTACCAAAACCAAAAGTAA

Sequence 15 (SEQ ID NO: 15):
ATGAGCGACAGCACAGTATATGTGCCTCCTCCCAACCCTGTATCCAAGGTTGTTGCCACGGATGC

GTATGTTAAACGCACCAACATATTTTATCACGCCAGCAGTTCTAGACTCCTTGCTGTGGGACATCC

ATATTACTCTATCAAAAAAGTTAACAAAACAGTTGTACCAAAGGTGTCTGGATATCAATATAGAG

TGTTTAAGGTAGTGTTGCCAGATCCTAACAAGTTTGCATTACCTGATTCATCTCTGTTTGACCCCA

CTACACAGCGTTTAGTATGGGCGTGCACAGGGTTGGAGGTAGGCAGGGGTCAACCTTTAGGCGTT

GGTGTTAGTGGGCATCCATTGCTAAACAAATATGATGATGTAGAAAATAGTGGTGGGTATGGTGG

TAATCCTGGTCAGGATAATAGGGTTAATGTAGGTATGGATTATAAACAAACCCAGCTATGTATGG

TGGGCTGTGCTCCACCGTTAGGTGAACATTGGGGTAAGGGTACACAATGTTCAAATACCTCTGTA

CAAAATGGTGACTGCCCCCCGTTGGAACTTATTACCAGTGTTATACAGGATGGGGACATGGTTGA

TACAGGCTTTGGTGCTATGAATTTTGCAGACTTACAAACCAATAAATCGGATGTTCCCCTTGATAT

TTGTGGAACTGTCTGCAAATATCCTGATTATTTGCAAATGGCAGCAGACCCTTATGGTGATAGGT

TGTTTTTTATTTGCGAAAGGAACAAATGTTTGCTAGACACTTTTTTAACAGGGCTGGCGAGGTGG

GGGAACCTGTGCCTGATACTCTTATAATTAAGGGTAGTGGAAATCGAACGTCTGTAGGGAGTAGT

ATATATGTACATACACCTAGTGGATCCTTGGTGTCTTCAGAGGCTCAATTATTTAATAAACCATAT

TGGCTTCAAAAGGCTCAGGGACATAACAATGGTATTTGCTGGGGAAACCACTTGTTTGTTACTGT

GGTAGATACCACACGCAGTACAAATATGACACTATGTGCATCTGTGTCTAAATCTGCTACATACA

CTAATTCAGATTATAAGGAATATATGCGCCATGTGGAGGAGTTTGATTTACAGTTTATTTTTCAAT

TGTGTAGCATTACATTATCTGCAGAAGTCATGGCCTATATACACACAATGAATCCTTCTGTTTTGG

AGGACTGGAACTTTGGTTTATCGCCTCCACCAAATGGTACACTGGAGGATACTTATAGATATGTA

CAGTCACAGGCCATTACCTGTCAGAAACCCACACCCGAAAAGAAAAACAGGACCCCTATAAGG

ATATGAGTTTTTGGGAGGTTAACTTAAAAGAAAAGTTTTCTTCTGAATTAGATCAGTTTCCCCTTG

-continued
```
GACGTAAGTTTTTATTGCAAAGTGGATATCGAGGACGGACGTCTGCTCGTACAGGTATAAAGCGC

CCAGCTGTGTCTAAGCCCTCTACAGCCCCCAAACGAAAACGTACCAAAACCAAAAGTAA
```

Sequence 16 (SEQ ID NO: 16):
```
ATGAGCGACAGCACAGTATATGTGCCTCCTCCCAACCCTGTATCCAAGGTTGTTGCCACGGATGC

GTATGTTAAACGCACCAACATATTTTATCACGCCAGCAGTTCTAGACTCCTTGCTGTGGGACATCC

ATATTACTCTATCAAAAAAGTTAACAAAACAGTTGTACCAAAGGTGTCTGGATATCAATATAGAG

TGTTTAAGGTAGTGTTGCCAGATCCTAACAAGTTTGCATTACCTGATTCATCTCTGTTTGACCCCA

CTACACAGCGTTTAGTATGGGCGTGCACAGGGTTGGAGGTAGGCAGGGGTCAACCTTTAGGCGTT

GGTGTTAGTGGGCATCCATTGCTAAACAAATATGATGATGTAGAAAATAGTGGTGGGTATGGTGG

TAATCCTGGTCAGGATAATAGGGTTAATGTAGGTATGGATTATAAACAAACCCAGCTATGTATGG

TGGGCTGTGCTCCACCGTTAGGTGAACATTGGGGTAAGGGTACACAATGTTCAAATACCTCTGTA

CAAAATGGTGACTGCCCCCCGTTGGAACTTATTACCAGTGTTATACAGGATGGGACATGGTTGA

TACAGGCTTTGGTGCTATGAATTTTGCAGACTTACAAACCAATAAATCGGATGTTCCCCTTGATAT

TTGTGGAACTGTCTGCAAATATCCTGATTATTTGCAAATGGCAGCAGACCCTTATGGTGATAGGT

TGTTTTTTTATTTGCGAAAGGAACAAATGTTTGCTAGACACTTTTTTAATAGGGCCGGTACTGTGG

GGGAACCTGTGCCTGATGACCTGTTGGTAAAAGGGGGTAATAATAGGTCATCTGTAGCTAGTAGT

ATTTATGTACATACACCTAGTGGATCCTTGGTGTCTTCAGAGGCTCAATTATTTAATAAACCATAT

TGGCTTCAAAAGGCTCAGGGACATAACAATGGTATTTGCTGGGGAAACCACTTGTTTGTTACTGT

GGTAGATACCACACGCAGTACAAATATGACACTATGTGCATCTGTAACTACATCTTCCACATACA

CCAATTCTGATTATAAGGAATATATGCGCCATGTGGAGGAGTTTGATTTACAGTTTATTTTTCAAT

TGTGTAGCATTACATTATCTGCAGAAGTCATGGCCTATATACACACAATGAATCCTTCTGTTTTGG

AGGACTGGAACTTTGGTTTATCGCCTCCACCAAATGGTACACTGGAGGATACTTATAGATATGTA

CAGTCACAGGCCATTACCTGTCAGAAACCCACACCCGAAAAAGAAAAACAGGACCCCTATAAGG

ATATGAGTTTTTGGGAGGTTAACTTAAAAGAAAAGTTTTCTTCTGAATTAGATCAGTTTCCCCTTG

GACGTAAGTTTTTATTGCAAAGTGGATATCGAGGACGGACGTCTGCTCGTACAGGTATAAAGCGC

CCAGCTGTGTCTAAGCCCTCTACAGCCCCCAAACGAAAACGTACCAAAACCAAAAGTAA
```

Sequence 35 (SEQ ID NO: 35):
KQCTNTPVQA

Sequence 36 (SEQ ID NO: 36):
TTSSTY

Sequence 37 (SEQ ID NO: 37):
FLNKYDDVENSGSGGNPGQDN

Specific Modes for Carrying Out the Invention

The present invention is further described by reference to the examples as follows, wherein the examples are used only for the purpose of illustrating the present invention, rather than limiting the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; and restriction enzymes are used under the conditions recommended by the manufacturers. Those skilled in the art understand that the examples are used for illustrating the present invention, but not intended to limit the protection scope of the present invention.

Example 1

Expression and Purification of the Mutated HPV11 L1 Proteins

Construction of Expression Vectors

An expression vector encoding the mutated HPV11 L1 protein (H11N4-6T1) comprising a specific segment from HPV6 L1 protein was constructed by PCR for multi-site mutagenesis, wherein the initial template used was the plasmid pTO-T7-HPV11N4C (encoding the HPV11 L1 protein having 4 amino acids truncated at N-terminal; abbreviated as 11L1N4 in Table 2). The templates and primers for each PCR were shown in Table 2, and the amplification conditions for PCR were as followed: denaturation at 94° C. for 10 min; 25 cycles (denaturation at 94° C. for 50 sec, annealing at a given temperature for a certain period of time, and extension at 72° C. for 7.5 min); and finally extension at 72° C. for 10 min. The sequences of the PCR primers used were listed in Table 3.

To the amplification product (50 μL), 2 μL restriction endonuclease DpnI was added, and the resultant mixture was incubated at 37° C. for 60 min. 10 μL of the product of digestion was used to transform 40 μL competent E. coli ER2566 (purchased from New England Biolabs) prepared by the Calcium chloride method. The transformed E. coli was spread onto solid LB medium (the components of the LB medium: 10 g/L peptone, 5 g/L yeast powder, 10 g/L NaCl, the same hereinafter) containing kanamycin (at a final concentration of 25 mg/mL, the same hereinafter), and was subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from E. coli, and T7 primer was used to sequence the nucleotide sequence of the fragment of interest inserted into the plasmids. The sequencing result showed that the nucleotide sequence of the fragment of interest inserted into the constructed plasmids (expression vectors) was SEQ ID NO: 12, and its encoded amino acid sequence was SEQ ID NO: 5 (the corresponding protein was designated as H11N4-6T1). The mutated protein H11N4-6T1 differs from HPV11N4 by: the substitution of the amino acid residues from positions 49 to 63 of wild type HPV11 L1 protein with the amino acid residues from positions 49 to 63 of wild type HPV6 L1 protein.

Gibson assembly (Gibson D G, Young L, Chuang R Y, Venter J C, Hutchison C A, Smith H O. Enzymatic assembly of DNA molecules up to several hundred kilobases. Nat Methods. 2009; 6:343-5. doi: 10.1038/nmeth.1318) was used to construct the expression vector encoding other mutated HPV11 L1 proteins, wherein the mutated HPV11 L1 proteins comprised a specific segment from HPV6 L1. In brief, a short fragment comprising mutations and a long fragment comprising no mutation were obtained by PCR, and Gibson assembly system was then used to ligate the two fragments to form a ring. The initial template used comprised the plasmid pTO-T7-HPV11N4C and the plasmid pTO-T7-HPV6N5C (encoding the HPV6 L1 protein having 5 amino acids truncated at N-terminal; abbreviated as 6L1N5 in Table 2). The templates and primers for each PCR were shown in Table 2, and, the amplification conditions for PCR for amplifying the short fragment were as followed: denaturation at 94° C. for 10 min; 25 cycles (denaturation at 94° C. for 50 sec, annealing at a given temperature for a certain period of time, and extension at 72° C. for 1 min); and finally extension at 72° C. for 10 min. The amplification conditions for PCR for amplifying the long fragment were as followed: denaturation at 94° C. for 10 min; 25 cycles (denaturation at 94° C. for 50 sec, annealing at a given temperature for a certain period of time, and extension at 72° C. for 7.5 min); and finally extension at 72° C. for 10 min. The sequences of the PCR primers used were listed in Table 3. The amplification product was subjected to electrophoresis, the fragment of interest was then recovered by using DNA Extraction Kit, and its concentration was determined. The short fragment and long fragment obtained by amplification were mixed at a molar ratio of 2:1 (a total volume of 3 μL), and 3 μL of 2× Gibson Assembly Master Mix (purchased from NEB, containing T5 exonuclease, Phusion DNA polymerase, Taq DNA ligase) was then added, and reacted at 50° C. for 1 h.

The assembled product (6 μL) was used to transform 40 μL competent *E. coli* ER2566 (purchased from New England Biolabs) prepared by the Calcium chloride method. The transformed *E. coli* were spread onto solid LB medium containing kanamycin, and were subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 13, 14, 15 and 16, respectively, and their encoded amino acid sequences were SEQ ID NO: 6, 7, 8 and 9, respectively (the corresponding proteins were designated as H11N4-6T2, H11N4-6T3, H11N4-6T4, and H11N4-6T5, respectively).

The mutated protein H11N4-6T2 differs from HPV11N4 by: the substitution of the amino acid residues from positions 119 to 140 of wild type HPV11 L1 protein with the amino acid residues from positions 119 to 139 of wild type HPV6 L1 protein. The mutated protein H11N4-6T3 differs from HPV11N4 by: the substitution of the amino acid residues from positions 170 to 179 of wild type HPV11 L1 protein with the amino acid residues from positions 169 to 178 of wild type HPV6 L1 protein. The mutated protein H11N4-6T4 differs from HPV11N4 by: the substitution of the amino acid residues from positions 257 to 288 of wild type HPV11 L1 protein with the amino acid residues from positions 256 to 287 of wild type HPV6 L1 protein. The mutated protein H11N4-6T5 differs from HPV11N4 by: the substitution of the amino acid residues from positions 346 to 351 of wild type HPV11 L1 protein with the amino acid residues from positions 345 to 350 of wild type HPV6 L1 protein.

TABLE 2

PCR templates and primes for constructing expression vectors

| Template | Upstream primer | Downstream primer | Product |
|---|---|---|---|
| 11L1N4 | H11N4-6T1-F | H11N4-6T1-R | H11N4-6T1 |
| 6L1N5 | G-H11N4-6T2-F | G-H11N4-6T2-R | H11N4-612-short fragment |
| 11L1N4 | G-V-H11N4-6T2-F | G-V-H11N4-6T2-R | H11N4-6T2-long fragment |
| 6L1N5 | G-H11N4-6T3-F | G-H11N4-6T3-R | H11N4-6T3-short fragment |
| 11L1N4 | G-V-H11N4-6T3-F | G-V-H11N4-6T3-R | H11N4-6T3-long fragment |
| 6L1N5 | G-H11N4-6T4-F | G-H11N4-6T4-R | H11N4-6T4-short fragment |
| 11L1N4 | G-V-H11N4-6T4-F | G-V-H11N4-6T4-R | H11N4-6T4-long fragment |
| 6L1N5 | G-H11N4-6T5-F | G-H11N4-6T5-R | H11N4-6T5-short fragment |
| 11L1N4 | G-V-H11N4-6T5-F | G-V-H11N4-6T5-R | H11N4-6T5-long fragment |

TABLE 3

Sequences of the primers used
(SEQ ID NOs: 17-34)

| SEQ ID NO: | Primer name | Primer sequence (5'-3') |
|---|---|---|
| 17 | H11N4-6T1-F | GTGGGACATCCATATTTTCTATCAAACGGGCTAACAAAACAGTTGTAC |
| 18 | H11N4-6T1-R | GTACAACTGTTTTGTTAGCCCGTTTGATAGAAAAATATGGATGTCCCAC |
| 19 | G-H11N4-6T2-F | TCAATATAGAGTGTTTAAGGTAGTGTTACCAGATCCTAACAAATTTGC |
| 20 | G-H11N4-6T2-R | CCCACCATACATAGCTGGGTTTGTTTATAATCCATACCAACAT |
| 21 | G-V-H11N4-6T2-F | AAACAAACCCAGCTATGTATGGTGG |
| 22 | G-V-H11N4-6T2-R | CACTACCTTAAACACTCTATATTGAT |
| 23 | G-H11N4-6T3-F | CTGTACAGAATGGTGACTGCCCGCCCTTAG |
| 24 | G-H11N4-6T3-R | AACACTGTGTACCTTTACCCCAATGCTCGC |
| 25 | G-V-H11N4-6T3-F | TAATACATCTGTACAGAATGGTGACTGCCCGCCCTTAG |
| 26 | G-V-H11N4-6T3-R | GATGTATTAGAACACTGTGTACCTTTACCCCAATGCTCG |
| 27 | G-H11N4-6T4-F | GGAACAAATGTTTGCTAGACACTTTTTTAACAGGGCTGGCGAGGTGG |
| 28 | G-H11N4-6T4-R | ACCAAGGATCCACTAGGTGTATGAACATATATACTCTCCCTACAG |
| 29 | G-V-H11N4-6T4-F | CATACACCTAGTGGATCCTTGG |
| 30 | G-V-H11N4-6T4-R | AAAGTGTCTAGCAAACATTTGTTCCT |
| 31 | G-H11N4-6T5-F | TGGTATTTGCTGGGGAAACCACCTGTTTGTTACTGTGGTAGATAC |
| 32 | G-H11N4-6T5-R | GAAAAATAAACTGTAAATCAAACTCTTCCACATGACGCATGTACTC |
| 33 | G-V-H11N4-6T5-F | TTTGATTTACAGTTTATTTTTC |
| 34 | G-V-H11N4-6T5-R | GTGGTTTCCCCAGCAAATACCATTG |

Expression of the Mutated Proteins on a Large Scale

The E. coli solutions comprising the recombinant plasmid pTO-T7-H11N4-6T1, pTO-T7-H11N4-6T2, pTO-T7-H11N4-6T3, pTO-T7-H11N4-6T4, and pTO-T7-H11N4-6T5, respectively, were taken from −70° C. refrigerator, seeded in 100 mL LB liquid medium containing kanamycin, and incubated at 200 rpm and 37° C. for about 8 h, respectively. Then, the culture was transferred to 500 mL LB medium containing kanamycin (1 ml bacterial solution was transferred), and was further incubated. When the bacterial concentration reached an $OD_{600}$ of about 0.6, the culturing temperature was lowered to 25° C. and 500 μL IPTG was added to each culture bottle. The incubation was further performed for 8 h. After the incubation was finished, the bacteria were collected by centrifugation. The bacteria expressing H11N4-6T1, H11N4-6T2, H11N4-6T3, H11N4-6T4 and H11N4-6T5 protein, were obtained, respectively.

Disruption of Bacteria Expressing the Mutated Proteins

The bacteria obtained were re-suspended at a ratio of 1 g bacteria to 10 mL lysis buffer (20 mM Tris buffer, pH7.2, 300 mM NaCl). The bacteria were disrupted by using an ultrasonic apparatus for 30 min. The lysis solution containing the disrupted bacteria were centrifuged at 13500 rpm (30000 g) for 15 min, and the supernatant (i.e. the supernatant of disrupted bacteria) was obtained.

Chromatographic Purification of the Mutated Proteins

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.), CHT-II (purchased from Bio-RAD) and Butyl Sepharose 4 Fast Flow (GE Healthcare Co.)

Buffer: 20 mM phosphate buffer, pH8.0, 20 mM DTT; and, 20 mM phosphate buffer, pH8.0, 20 mM DTT, 2M NaCl.

Sample: the supernatants of disrupted bacteria containing H11N4-6T1, H11N4-6T2, H11N4-6T3, H11N4-6T4 and H11N4-6T5, respectively, as obtained above.

Elution Protocol:

(1) Cation exchange purification of the supernatant of disrupted bacteria by SP Sepharose 4 Fast Flow: the sample was loaded on the column, undesired proteins were then eluted with a buffer containing 400 mM NaCl, followed by the elution of the protein of interest with a buffer containing 800 mM NaCl, and the fraction eluted with the buffer containing 800 mM NaCl was collected;

(2) Chromatographic purification of the elution fraction obtained in the step (1) by CHT-II (hydroxyapatite chromatography): the elution fraction obtained in the step (1) was diluted so that the NaCl concentration was decreased to 0.5 M; the sample was loaded on the column, undesired proteins were then eluted with a buffer containing 500 mM NaCl, followed by the elution of the protein of interest with a buffer containing 1000 mM NaCl, and the fraction eluted with the buffer containing 1000 mM NaCl was collected;

(3) Chromatographic purification of the elution fraction obtained in the step (2) by HIC (hydrophobic interaction chromatography): the sample was loaded on the column, undesired proteins were then eluted with a buffer containing 1000 mM NaCl, followed by the elution of the protein of interest with a buffer containing 200 mM NaCl, and the fraction eluted with the buffer containing 200 mM NaCl was collected.

150 μL elution fraction obtained in the step (3) was added to 30 μL, of 6× Loading Buffer. The resultant solution was mixed homogeneously and incubated in 80° C. water bath for 10 min. 10 μl of the resultant sample was then subjected to 10% SDS-PAGE at 120V for 120 min; and the electrophoretic bands were stained by Coomassie brilliant blue. The electrophoretic result was shown in FIG. 1. The result showed that after said purification steps, H11N4-6T1, H11N4-6T2, H11N4-6T3, H11N4-6T4 and H11N4-6T5 protein had a purity of above 95%.

By similar methods, HPV11N4 protein was prepared and purified by using *E. coli* and the plasmid pTO-T7-

HPV11N4C; HPV6N5 protein was prepared and purified by using E. coli and the plasmid pTO-T7-HPV6N5C.

Example 2

Assembly of HPV Virus-Like Particles and Morphological Test of Particles

Assembly of HPV Virus-Like Particles

A given volume (about 2 ml) of the protein H11N4-6T1, H11N4-6T2, H11N4-6T3, H11N4-6T4 or H11N4-6T5, was dialyzed to (1) 2 L storage buffer (20 mM sodium phosphate buffer pH 6.5, 0.5 M NaCl); (2) 2 L renaturation buffer (50 mM sodium phosphate buffer pH 6.0, 2 mM CaCl2, 2 mM MgCl2, 0.5 M NaCl); and (3) 20 mM sodium phosphate buffer pH 7.0, 0.5 M NaCl, successively. The dialysis was performed in each of the three buffers for 12 h.

By similar methods, the HPV11N4 and HPV6N5 protein were assembled into HPV11N4 VLP and HPV6N5 VLP, respectively.

Molecular Sieve Chromatographic Analysis

The dialyzed sample was subjected to molecular sieve chromatographic analysis by 1120 Compact LC High Performance Liquid Chromatographic System (Agilent Technologies), wherein the analytical column used was TSK Gel PW5000xl 7.8×300 mm. The analysis results were shown in FIGS. 2A-2F. The results showed that the first protein peak of the samples comprising the protein H11N4-6T1, H11N4-6T2, H11N4-6T3, H11N4-6T4 and H11N4-6T5 respectively appeared at about 12 min, which was comparable to that of HPV11N4 VLP. This showed that the proteins prepared above were able to assemble into VLPs.

Sedimentation Velocity Analysis

The apparatus for sedimentation velocity analysis was Beckman XL-A Analytical Ultracentrifuge, equipped with optical inspection system and An-50Ti and An-60Ti rotor. The sedimentation coefficient of HPV11N4 VLP, H11N4-6T1 VLP, H11N4-6T2 VLP, H11N4-6T3 VLP, H11N4-6T4 VLP and H11N4-6T5 VLP was analyzed by sedimentation velocity method. The results were shown in FIGS. 3A-3F. The results showed that the sedimentation coefficient of H11N4-6T1 VLP, H11N4-6T2 VLP, H11N4-6T3 VLP, H11N4-6T4 VLP and H11N4-6T5 VLP was 140S, 138S, 111S, 139S and 139S, respectively. This showed that said 5 mutated HPV11 L1 proteins were able to assemble into virus-like particles that were similar to wild type VLP (HPV11N4 VLP, 136.3S) in terms of size and morphology.

Morphological Test of Virus-Like Particles

A 100 µL sample comprising VLP was observed by transmission electron microscope (TEM). The equipment used was a 100 kV Transmission Electron Microscope supplied by JEOL Ltd. (100,000× magnification). In brief, a 13.5 µL sample was negatively stained with 2% phosphotungstic acid (pH 7.0), fixed on a carbon-coated copper grid, and then observed by TEM. The results were shown in FIGS. 4A-4F. The result showed that H11N4-6T1, H11N4-6T2, H11N4-6T3, H11N4-6T4 and H11N4-6T5 were able to assemble into virus-like particles. In addition, the results also showed that the particles assembled by these mutated proteins had a radius of about 25 nm, and were uniform in size. This indicated that these mutated proteins were similar to wild type HPV11 L1 protein (HPV11N4 VLP), and were able to assemble into VLPs with a uniform size.

Example 3

Evaluation of Thermostability of Virus-Like Particles

The VLPs formed by HPV11N4, H11N4-6T1, H11N4-6T2, H11N4-6T3, H11N4-6T4 and H11N4-6T5 were evaluated for their thermostability by using differential scanning calorimeter VP Capillary DSC purchased from GE Company (i.e. the original MicroCal Co.), wherein the storage buffer for the protein was used as control, and the proteins were scanned at a heating rate of 1.5° C./min within a temperature range of 10° C.-90° C. The detection results were shown in FIGS. 5A-5F. The results showed that all these VLPs formed by the proteins had very high thermostability.

Example 4

Figure 6:
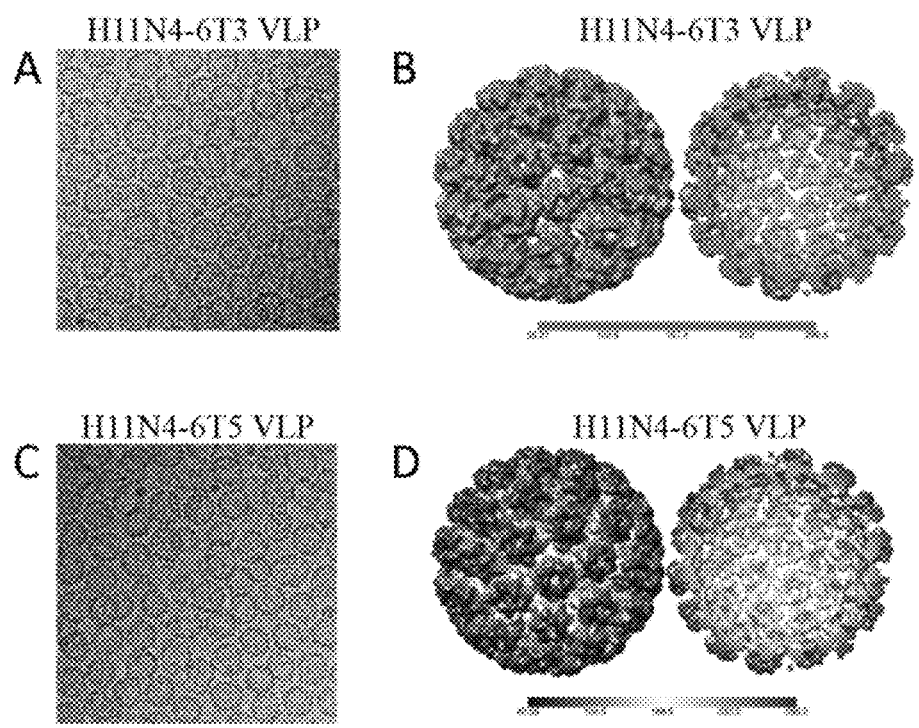

Reconstruction of Three-Dimensional Structures of H11N4-6T3 VLP and H11N4-6T5 VLP In accordance with the previously reported method (Wolf M, Garcea R L, Grigorieff N. et al. Proc Natl Acad Sci USA. (2010), 107(14): 6298-303), the three-dimensional structures of H11N4-6T3 VLP and H11N4-6T5 VLP were reconstructed by using cryo-electron microscopy (cryoEM). In brief, cryo-electron microscopy (cryoEM) was used to observe H11N4-6T3 VLP and H11N4-6T5 VLP, and then in the cryo-electron microscopy (cryoEM) photographs of H11N4-6T3 VLP and H11N4-6T5 VLP (FIGS. 6A and 6C), 300 particles and 360 particles with an uniform size and a diameter of greater than 50 nm were selected for computer overlapping and structural reconstruction, respectively, thereby obtaining the three-dimensional structures of H11N4-6T3 VLP and H11N4-6T5 VLP. The three-dimensional structures obtained were shown in FIGS. 6B and 6D (at a resolution of 17.38 Å and 20.48 Å, respectively). The results showed that both H11N4-6T3 VLP and H11N4-6T5 VLP had a T=7 icosahedral structure (h=1, k=2) consisting of 72 capsomers (morphological subunit, pentamer). Unlike conventional icosahedral viral capsids consistent with quasi-equivalence principle, all the constitutive subunits in the structures of H11N4-6T3 VLP and H11N4-6T5 VLP were pentamers, without hexamer. Moreover, said VLPs had an external diameter of about 60 nm. These were similar to the three-dimensional structures of the previously reported natural HPV viral particles and the HPV VLP prepared by eukaryotic expression system (e.g. poxvirus expression system) (Baker T S, Newcomb W W, Olson N H. et al. Biophys J. (1991), 60(6): 1445-1456. Hagensee M E, Olson N H, Baker T S, et al. J Virol. (1994), 68(7):4503-4505. Buck C B, Cheng N, Thompson C D. et al. J Virol. (2008), 82(11): 5190-7).

Example 5

Evaluation of Immune Protection of Virus-Like Particles in Animals

The immune protection of the VLPs formed by H11N4-6T1, H11N4-6T2, H11N4-6T3, H11N4-6T4 and H11N4-6T5, was evaluated in mice. Animals for vaccination were BALB/c mice (ordinary grade), 5-6 weeks old (purchased from Shanghai SLAC Laboratory Animal Co. LTD.).

Figure 7:
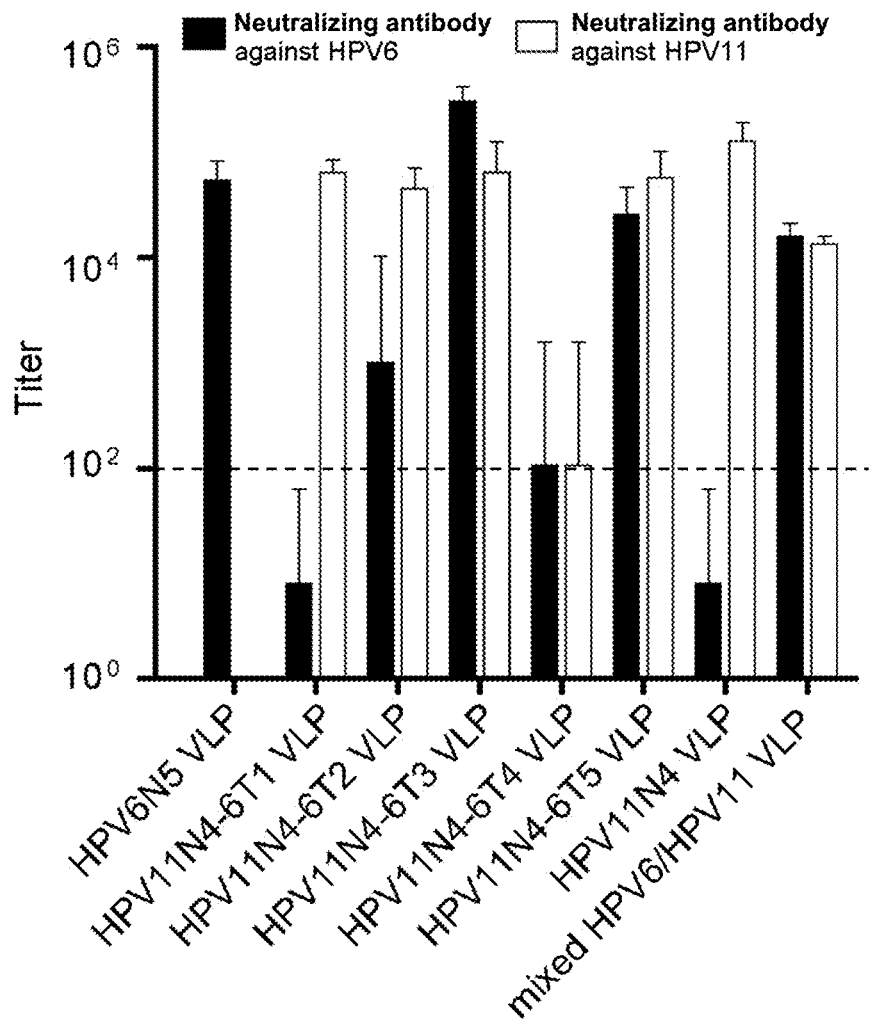
FIG. 7 shows the evaluation result of immune protection of the Experimental groups H11N4-6T1, H11N4-6T2, H11N4-6T3, H11N4-6T4 and H11N4-6T5, and the Control groups HPV11N4 VLP, HPV6N5 VLP and a mixed HPV11/HPV6 VLP in mice. The result showed that either of H11N4-6T3 VLP and H11N4-6T5 VLP could induce the generation of high-titer neutralizing antibodies against HPV11 and HPV6 in mice; and their protective effects against HPV11 were comparable to that of HPV11N4 VLP alone or the mixed HPV11/HPV6 VLP, and were significantly higher than that of HPV6N5 VLP alone; and their protective effects against HPV6 were comparable to that of HPV6N5 VLP alone or the mixed HPV11/HPV6 VLP, and were significantly higher than that of HPV11N4 VLP alone. H11N4-6T2 VLP could also induce the generation of high-titer neutralizing antibodies against HPV11 and HPV6 in mice, but its ability of inducing the generation of neutralizing antibodies against HPV6 was weaker than that of H11N4-6T3 VLP and H11N4-6T5 VLP. These results showed that H11N4-6T2 VLP, H11N4-6T3 VLP and H11N4-6T5 VLP could be used as effective vaccines for preventing HPV11 infection and HPV6 infection, and could be used in place of a mixed vaccine comprising HPV11 VLP and HPV6 VLP.

The HPV11N4 VLP, HPV6N5 VLP, H11N4-6T1 VLP, H11N4-6T2 VLP, H11N4-6T3 VLP, H11N4-6T4 VLP, H11N4-6T5 VLP and a mixed HPV11/HPV6 VLP (i.e. a mixture of HPV11N4 VLP and HPV6N5 VLP) as prepared above were absorbed onto aluminum adjuvant, respectively. Mice were divided into 8 groups depending on immunogen, and each group included 4 mice. Vaccination procedure was as followed: the first vaccination at Week 0, and the booster vaccination at Weeks 2 and 4, respectively. Mice were vaccinated via subcutaneous injection. The immunogens used and doses thereof were shown in Table 4. At Week 8 after the first vaccination, venous blood was collected from eyeball, and serum was separated. The titers of neutralizing antibodies in the serum were determined. The detection result was shown in FIG. 7. The result showed that either of H11N4-6T3 VLP and H11N4-6T5 VLP could induce the generation of high-titer neutralizing antibodies against HPV11 and HPV6 in mice; and their protective effects against HPV11 were comparable to that of HPV11N4 VLP alone or the mixed HPV11/HPV6 VLP, and were significantly higher than that of HPV6N5 VLP alone; and their protective effects against HPV6 were comparable to that of HPV6N5 VLP alone or the mixed HPV11/HPV6 VLP, and were significantly higher than that of HPV11N4 VLP alone. H11N4-6T2 VLP could induce the generation of high-titer neutralizing antibodies against HPV11 and HPV6 in mice, but its ability of inducing the generation of neutralizing antibodies against HPV6 was weaker than that of H11N4-6T3 VLP and H11N4-6T5 VLP. These results showed that H11N4-6T2 VLP, H11N4-6T3 VLP and H11N4-6T5 VLP could be used as effective vaccines for preventing HPV11 infection and HPV6 infection, and could be used in place of a mixed vaccine comprising HPV11 VLP and HPV6 VLP.

TABLE 4

Vaccination schedule

| Antigen for vaccination | Adjuvant | Immunizing dose | Number | Vaccination procedure (week) |
| --- | --- | --- | --- | --- |
| HPV6N5 VLP | aluminum adjuvant | 5 µg | 4 | 0, 2, 4 |
| HPV11N4 VLP | aluminum adjuvant | 5 µg | 4 | 0, 2, 4 |
| mixed HPV11/ HPV6 VLP | aluminum adjuvant | 10 µg (5 µg for each VLP) | 4 | 0, 2, 4 |
| H11N4-6T1 VLP | aluminum adjuvant | 5 µg | 4 | 0, 2, 4 |
| H11N4-6T2 VLP | aluminum adjuvant | 5 µg | 4 | 0, 2, 4 |
| H11N4-6T3 VLP | aluminum adjuvant | 5 µg | 4 | 0, 2, 4 |
| H11N4-6T4 VLP | aluminum adjuvant | 5 µg | 4 | 0, 2, 4 |
| H11N4-6T5 VLP | aluminum adjuvant | 5 µg | 4 | 0, 2, 4 |

Example 6

Evaluation of Neutralizing Antibody Titer in Serum of Mice Vaccinated with VLP

In this experiment, vaccination schedule was shown in Table 5. All the mice (6-week old BalB/c female mice) were divided into 3 groups: Aluminum adjuvant group 1 (at an immunizing dose of 10 µg, using aluminum adjuvant), Aluminum adjuvant group 2 (at an immunizing dose of 1 µg, using aluminum adjuvant), and Aluminum adjuvant group 3 (at an immunizing dose of 0.1 µg, using aluminum adjuvant). Each group was further divided into 5 subgroups. The Control subgroups 1-3 were vaccinated with HPV11N4 VLP alone, HPV6N5 VLP alone and a mixed HPV11/HPV6 VLP (i.e. a mixture of HPV11N4 VLP and HPV6N5 VLP, wherein each VLP was administered at a given immunizing dose), respectively, and the Experimental subgroups 1-2 were vaccinated with H11N4-6T3 VLP and H11N4-6T5 VLP, respectively.

Figure 8:
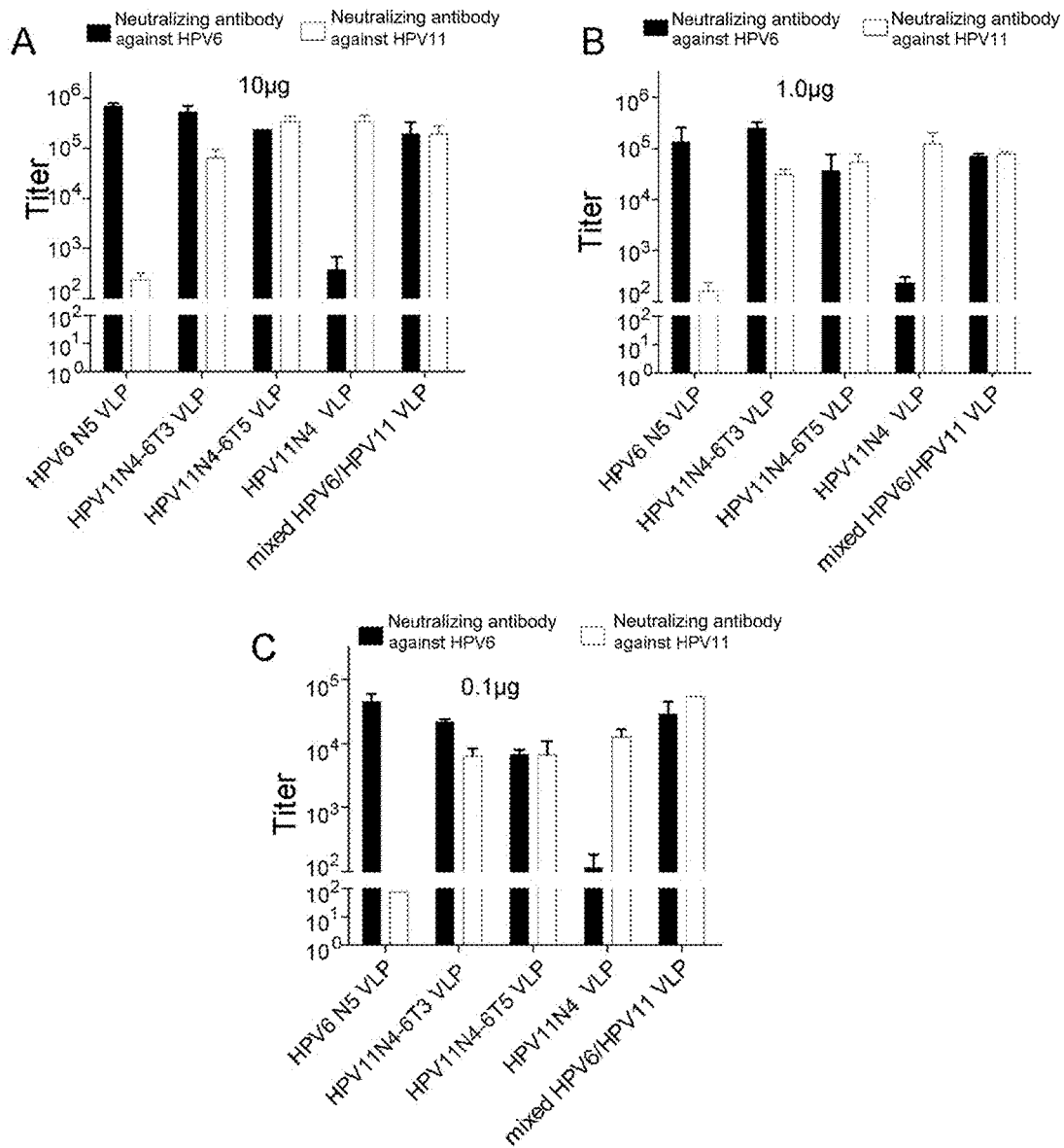
FIGS. 8A-8C show the evaluation results of neutralizing antibody titer in mouse serum after vaccination of mice with H11N4-6T3 VLP and H11N4-6T5 VLP respectively.

6 mice/subgroup were vaccinated by intraperitoneal injection, at an immunizing dose of 10 µg, 1 µg, 0.1 µg, respectively, and an injection volume of 1 ml. All the mice were subjected to the first vaccination at Week 0, and then subjected to the booster vaccination at Weeks 2 and 4, respectively. At Week 8, blood sample was collected via orbital bleeding, and the titers of antibodies against HPV11 and HPV6 in serum were analyzed. The analysis results were shown in FIGS. 8A-8C. The results showed that either of H11N4-6T3 VLP and H11N4-6T5 VLP could induce the generation of high-titer neutralizing antibodies against HPV11 in mice, and their protective effects were comparable to that of HPV11N4 VLP alone or the mixed HPV11/HPV6 VLP at the same dose, and were significantly superior to that of HPV6N5 VLP alone at the same dose; and they could induce the generation of high-titer neutralizing antibodies against HPV6 in mice, and their protective effects were comparable to that of HPV6N5 VLP alone or the mixed HPV11/HPV6 VLP at the same dose, and were significantly superior to that of HPV11N4 VLP alone at the same dose. This showed that H11N4-6T3 VLP and H11N4-6T5 VLP had good cross-immunogenicity and cross-protection against HPV11 and HPV6.

TABLE 5

Vaccination schedule

| Group | Antigen for vaccination | Adjuvant | Immunizing dose | Number | Vaccination procedure (week) |
| --- | --- | --- | --- | --- | --- |
| Aluminum adjuvant group 1 | HPV11N4 VLP | aluminum adjuvant | 10 µg | 6 | 0, 2, 4 |
| | HPV6N5 VLP | aluminum adjuvant | 10 µg | 6 | 0, 2, 4 |
| | a mixed HPV11/HPV6 VLP | aluminum adjuvant | 10 µg for each | 6 | 0, 2, 4 |

TABLE 5-continued

Vaccination schedule

| Group | Antigen for vaccination | Adjuvant | Immunizing dose | Number | Vaccination procedure (week) |
|---|---|---|---|---|---|
| | H11N4-6T3 VLP | aluminum adjuvant | 10 μg | 6 | 0, 2, 4 |
| | H11N4-6T5 VLP | aluminum adjuvant | 10 μg | 6 | 0, 2, 4 |
| Aluminum adjuvant Group 2 | HPV11N4 VLP | aluminum adjuvant | 1 μg | 6 | 0, 2, 4 |
| | HPV6N5 VLP | aluminum adjuvant | 1 μg | 6 | 0, 2, 4 |
| | a mixed HPV11/HPV6 VLP | aluminum adjuvant | 1 μg for each | 6 | 0, 2, 4 |
| | H11N4-6T3 VLP | aluminum adjuvant | 1 μg | 6 | 0, 2, 4 |
| | H11N4-6T5 VLP | aluminum adjuvant | 1 μg | 6 | 0, 2, 4 |
| Aluminum adjuvant group 3 | HPV11N4 VLP | aluminum adjuvant | 0.1 μg | 6 | 0, 2, 4 |
| | HPV6N5 VLP | aluminum adjuvant | 0.1 μg | 6 | 0, 2, 4 |
| | a mixed HPV11/HPV6 VLP | aluminum adjuvant | 0.1 μg for each | 6 | 0, 2, 4 |
| | H11N4-6T3 VLP | aluminum adjuvant | 0.1 μg | 6 | 0, 2, 4 |
| | H11N4-6T5 VLP | aluminum adjuvant | 0.1 μg | 6 | 0, 2, 4 |

Example 7

Evaluation of ED50 of VLP for Inducing Seroconversion 6-week old BalB/c female mice (8 mice) were vaccinated with aluminum adjuvant by single intraperitoneal injection, wherein H11N4-6T3 VLP or H11N4-6T5 VLP (at an immunizing dose of 0.300 μg, 0.100 μg, 0.033 μg or 0.011 μg) was used in the Experimental groups; and HPV6N5 VLP alone or HPV11N4 VLP alone (at an immunizing dose of 0.300 μg, 0.100 μg, 0.033 μg or 0.011 μg), or a mixed HPV11/HPV6 VLP (i.e. a mixture of HPV6N5 VLP and HPV11N4 VLP, wherein the immunizing dose for each VLP was 0.300 μg, 0.100 μg, 0.033 μg, 0.011 μg or 0.004 μg) was used in the Control groups; and the immunizing volume was 1 mL. In addition, the diluent for diluting a vaccine was used as blank control. 8 Mice were vaccinated in each group, and at Week 5 after vaccination, serum was collected. Later, the neutralizing antibody titer of serum was determined by neutralization test, and by Reed-Muench method (Reed L J M H. A simple method of estimating fifty percent endpoints. Am J Hyg. 1938; 27:493-7), $ED_{50}$ for inducing seroconversion (i.e. inducing the generation of antibodies in mice) was calculated for each sample. The results were shown in Tables 6.1-6.5.

TABLE 6.1

$ED_{50}$ of HPV6N5 VLP for inducing antibodies against HPV6 and HPV11 (seroconversion) in mice

| Antibody | Immunizing dose (μg) | Total number of mice | Number of mice with positive conversion | Positive conversion rate | $ED_{50}$ (μg) |
|---|---|---|---|---|---|
| Antibody against HPV6 | 0.300 | 8 | 7 | 92.31% | 0.090 |
| | 0.100 | 8 | 5 | 55.56% | |
| | 0.033 | 8 | 0 | 0.00% | |
| | 0.011 | 8 | 0 | 0.00% | |

TABLE 6.1-continued $ED_{50}$ of HPV6N5 VLP for inducing antibodies against HPV6 and HPV11 (seroconversion) in mice

| Antibody | Immunizing dose (μg) | Total number of mice | Number of mice with positive conversion | Positive conversion rate | $ED_{50}$ (μg) |
|---|---|---|---|---|---|
| Antibody against HPV11 | 0.300 | 8 | 1 | 22.22% | >0.3 |
| | 0.100 | 8 | 0 | 6.25% | |
| | 0.033 | 8 | 1 | 4.35% | |
| | 0.011 | 8 | 0 | 0.00% | |

TABLE 6.2

$ED_{50}$ of H11N4-6T3 VLP for inducing antibodies against HPV6 and HPV11 (seroconversion) in mice

| Antibody | Immunizing dose (μg) | Total number of mice | Number of mice with positive conversion | Positive conversion rate | $ED_{50}$ (μg) |
|---|---|---|---|---|---|
| Antibody against HPV6 | 0.300 | 8 | 8 | 100.00% | 0.025 |
| | 0.100 | 8 | 7 | 92.86% | |
| | 0.033 | 8 | 6 | 66.67% | |
| | 0.011 | 8 | 0 | 0.00% | |
| Antibody against HPV11 | 0.300 | 8 | 8 | 100.00% | 0.073 |
| | 0.100 | 8 | 5 | 66.67% | |
| | 0.033 | 8 | 1 | 9.09% | |
| | 0.011 | 8 | 0 | 0.00% | |

TABLE 6.3

ED$_{50}$ of H11N4-6T5 VLP for inducing antibodies against HPV6 and HPV11 (seroconversion) in mice

| Antibody | Immunizing dose (μg) | Total number of mice | Number of mice with positive conversion | Positive conversion rate | ED$_{50}$ (μg) |
|---|---|---|---|---|---|
| Antibody against HPV6 | 0.300 | 8 | 4 | 66.67% | 0.180 |
| | 0.100 | 8 | 3 | 30.70% | |
| | 0.033 | 8 | 1 | 5.88% | |
| | 0.011 | 8 | 0 | 0.00% | |
| Antibody against HPV11 | 0.300 | 8 | 6 | 81.82% | 0.189 |
| | 0.100 | 8 | 2 | 27.27% | |
| | 0.033 | 8 | 0 | 5.88% | |
| | 0.011 | 8 | 1 | 4.17% | |

TABLE 6.4

ED$_{50}$ of HPV11N4 VLP for inducing antibodies against HPV6 and HPV11 (seroconversion) in mice

| Antibody | Immunizing dose (μg) | Total number of mice | Number of mice with positive conversion | Positive conversion rate | ED$_{50}$ (μg) |
|---|---|---|---|---|---|
| Antibody against HPV6 | 0.300 | 8 | 3 | 44.44% | >0.3 |
| | 0.100 | 8 | 1 | 7.69% | |
| | 0.033 | 8 | 0 | 0.00% | |
| | 0.011 | 8 | 0 | 0.00% | |
| Antibody against HPV11 | 0.300 | 8 | 8 | 100.00% | 0.044 |
| | 0.100 | 8 | 7 | 91.67% | |
| | 0.033 | 8 | 2 | 36.36% | |
| | 0.011 | 8 | 2 | 13.33% | |

TABLE 6.5

ED$_{50}$ of a mixed HPV11/HPV6 VLP for inducing antibodies against HPV6 and HPV11 (seroconversion) in mice

| Antibody | Immunizing dose (μg) | Total number of mice | Number of mice with positive conversion | Positive conversion rate | ED$_{50}$ (μg) |
|---|---|---|---|---|---|
| Antibody against HPV6 | 0.300 for each VLP | 8 | 7 | 95.24% | 0.033 |
| | 0.100 for each VLP | 8 | 8 | 92.86% | |
| | 0.033 for each VLP | 8 | 4 | 50.00% | |
| | 0.011 for each VLP | 8 | 1 | 7.69% | |
| Antibody against HPV11 | 0.300 for each VLP | 8 | 7 | 95.65% | 0.023 |
| | 0.100 for each VLP | 8 | 8 | 93.75% | |
| | 0.033 for each VLP | 8 | 6 | 70.00% | |
| | 0.011 for each VLP | 8 | 1 | 9.09% | |

The results showed that ED$_{50}$ of H11N4-6T3 VLP and H11N4-6T5 VLP for inducing the generation of antibodies against HPV6 in mice was comparable to that of HPV6N5 VLP alone and that of the mixed HPV11/HPV6 VLP, and was significantly superior to that of HPV11N4 VLP alone; and, ED$_{50}$ of H11N4-6T3 VLP and H11N4-6T5 VLP for inducing the generation of antibodies against HPV11 in mice was comparable to that of HPV11N4 VLP alone and that of the mixed HPV11/HPV6 VLP, and was significantly superior to that of HPV6N5 VLP alone. This further showed that H11N4-6T3 VLP and H11N4-6T5 VLP had good cross-immunogenicity and cross-protection against HPV6 and HPV11.

Example 8

Evaluation of Immune Protection of H11N4-6T3 VLP and H11N4-6T5 VLP in Cynomolgus Monkey 18 Cynomolgus monkeys with a similar body weight were randomly divided into 3 groups (6 monkeys for each group), wherein, monkeys in Group 1 were vaccinated with 5 μg H11N4-6T3 VLP; monkeys in Group 2 were vaccinated with 5 μg H11N4-6T5 VLP; and monkeys in Group 3 were vaccinated with 10 μg mixed HPV11/HPV6 VLP (5 μg HPV6N5 VLP+5 μg HPV11N4 VLP). The adjuvant used was aluminum adjuvant, the injection volume was 1 ml, and the monkeys were vaccinated by intramuscular injection. Vaccination schedule was shown in Table 7.

Figure 9:
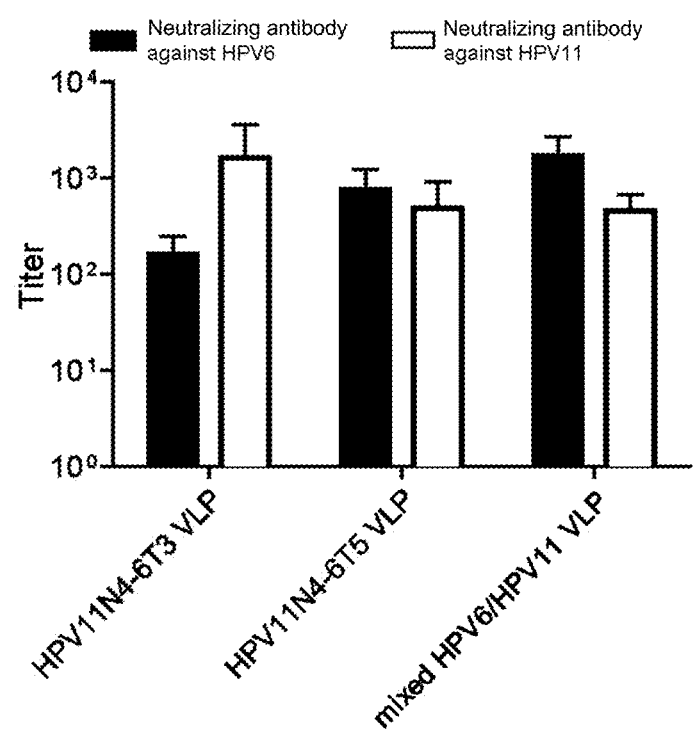
FIG. 9 shows the evaluation result of neutralizing antibodies in cynomolgus monkey serum after vaccination of cynomolgus monkeys with H11N4-6T3 VLP or H11N4-6T5 VLP. The result showed that either of H11N4-6T3 VLP and H11N4-6T5 VLP could induce the generation of high-titer neutralizing antibodies against HPV11 and HPV6 in cynomolgus monkeys, and their protective effects were comparable to that of the mixed HPV11/HPV6 VLP. This showed that H11N4-6T3 VLP and H11N4-6T5 VLP had good cross-immunogenicity and cross-protection against HPV11 and HPV6.

Two months after vaccination, venous blood was collected, and the neutralizing antibody titer of serum was determined by neutralization test. The experimental result was shown in FIG. 9. The result showed that either of H11N4-6T3 VLP and H11N4-6T5 VLP could induce the generation of neutralizing antibodies against HPV11 and HPV6 in cynomolgus monkeys; and the titer of the neutralizing antibodies induced by them was comparable to the titer of the neutralizing antibodies induced by the mixed HPV11/HPV6 VLP. These results showed that both of H11N4-6T3 VLP and H11N4-6T5 VLP have good immunogenicity, and could induce cross-protection against HPV6 and HPV11 in cynomolgus monkey, and their protective effects against HPV11 and HPV6 were comparable to that of the mixed HPV11/HPV6 VLP. Therefore, H11N4-6T3 VLP and H11N4-6T5 VLP could be used to prevent infection by HPV6 and HPV11.

TABLE 7

Vaccination schedule for cynomolgus monkey

| Immunogen | Adjuvant | Immunizing dose | Vaccination Number | Vaccination procedure |
|---|---|---|---|---|
| a mixed HPV11/HPV6 VLP | aluminum adjuvant | 10 μg (5 μg for each VLP) | 6 | single injection |
| H11N4-6T3 VLP | aluminum adjuvant | 5 μg | 6 | single injection |
| H11N4-6T5 VLP | aluminum adjuvant | 5 μg | 6 | single injection |

Although the specific embodiments of the present invention have been described in details, those skilled in the art would understand that, according to the teachings disclosed in the specification, various modifications and changes can be made thereto, and that such modifications and changes are within the scope of the present invention. The scope of the present invention is given by the appended claims and any equivalents thereof.

The invention claimed is:

1. A mutated HPV11 L1 protein or a variant thereof, wherein as compared with a wild type HPV11 L1 protein, the mutated HPV11 L1 protein has the following mutations:
   (1) N-terminal truncation of 3, 4, 5 or 6 amino acids; and
   (2) (a) substitution of amino acid residues at positions 346-351 of the wild type HPV11 L1 protein with amino acid residues at the corresponding positions of a L1 protein of a wild-type HPV6; or
   (b) substitution of amino acid residues at positions 119-140 of the wild type HPV11 L1 protein with amino acid residues at the corresponding positions of a L1 protein of a wild type HPV6.

2. An isolated nucleic acid, encoding the mutated HPV11 L1 protein according to claim 1.

3. A vector comprising the isolated nucleic acid according to claim 2.

4. A host cell comprising the isolated nucleic acid according to claim 2 and/or a vector comprising the isolate nucleic acid.

5. A HPV virus-like particle, comprising the mutated HPV11 L1 protein according to claim 1.

6. A composition, comprising any of the following:

(i) the mutated HPV11 L1 protein according to claim 1, or (ii) an isolated nucleic acid encoding the mutated HPV11 L1 protein as described in part (i), or (iii) a vector comprising the isolated nucleic acid as described in part (ii), or (iv) a host cell comprising the isolated nucleic acid as described in part (ii) or the vector as described in part (iii), or (v) an HPV virus-like particle comprising the mutated HPV11 L1 protein as described in part (i).

7. A pharmaceutical composition or vaccine, comprising the HPV virus-like particle according to claim 5, and optionally a pharmaceutically acceptable carrier and/or excipient.

8. A method for preparing the mutated HPV11 L1 protein according to claim 1, comprising expressing the mutated HPV11 L1 protein in a host cell, and then recovering the mutated HPV11 L1 protein from a culture of the host cell.

9. A method for preparing a vaccine, comprising combining the HPV virus-like particle according to claim 5 with a pharmaceutically acceptable carrier and/or excipient.

10. A method for preventing HPV infection or a disease caused by HPV infection, comprising administering to a subject a prophylactically effective amount of the HPV virus-like particle according to claim 5 or a pharmaceutical composition or vaccine comprising the HPV virus-like particle according to claim 5 and optionally a pharmaceutically acceptable carrier and/or excipient.

11. The mutated HPV11 L1 protein according to claim 1, wherein the mutated HPV11 L1 protein has 4 amino acids truncated from the N-terminal, as compared with the wild type HPV11 L1 protein.

12. The mutated HPV11 L1 protein according to claim 1, wherein: the amino acid residues at the corresponding positions as described in (2) (a) are amino acid residues at positions 345-350 of a wild type HPV6 L1 protein; and/or, the amino acid residues at the corresponding positions as described in (2) (b) are amino acid residues at positions 119-139 of a wild type HPV6 L1 protein.

13. The mutated HPV11 L1 protein according to claim 1, wherein: the wild type HPV11 L1 protein has an amino acid sequence as set forth in SEQ ID NO: 1; and/or, the wild type HPV6 L1 protein has an amino acid sequence as set forth in SEQ ID NO: 2.

14. The mutated HPV11 L1 protein according to claim 1, wherein the mutated HPV11 L1 protein has an amino acid sequence selected from the group consisting of: SEQ ID NOs: 6 and 9.

15. The pharmaceutical composition or vaccine according to claim 7, wherein the HPV virus-like particle is present in an amount effective for preventing HPV infection or a disease caused by HPV infection.

16. The pharmaceutical composition or vaccine according to claim 15, wherein: the HPV infection is HPV11 infection and/or HPV6 infection; and/or, the disease caused by HPV infection is selected from the group consisting of cervical cancer and condyloma *acuminatum*.

17. The method according to claim 8, wherein the host cell is *E. coli*.

18. The method according to claim 8, wherein the method comprises the steps of: expressing the mutated HPV11 L1 protein in *E. coli*, and then obtaining the mutated HPV11 L1 protein by purifying a lysate supernatant of the *E. coli*.

19. The method according to claim 10, wherein: the HPV infection is an HPV11 infection and/or an HPV6 infection; and/or, the disease caused by the HPV infection is selected from the group consisting of cervical cancer and condyloma *acuminatum*.

\* \* \* \* \*